United States Patent
Staffler et al.

(10) Patent No.: US 9,029,327 B2
(45) Date of Patent: May 12, 2015

(54) VACCINE

(75) Inventors: Günther Staffler, Vienna (AT); Petra Lührs, Vienna (AT); Andreas Mairhofer, Vienna (AT); Frank Mattner, Vienna (AT); Walter Schmidt, Vienna (AT); Andrea Dolischka, Vienna (AT)

(73) Assignee: Affiris AG, Vienna (AT)

( * ) Notice: Subject to any disclaimer, the term of this patent is extended or adjusted under 35 U.S.C. 154(b) by 0 days.

(21) Appl. No.: 13/386,603

(22) PCT Filed: Jul. 23, 2010

(86) PCT No.: PCT/AT2010/000271
§ 371 (c)(1),
(2), (4) Date: Jan. 23, 2012

(87) PCT Pub. No.: WO2011/009152
PCT Pub. Date: Jan. 27, 2011

(65) Prior Publication Data
US 2012/0269836 A1  Oct. 25, 2012

(30) Foreign Application Priority Data
Jul. 23, 2009 (AT) ................. A 1162/2009

(51) Int. Cl.
| A61K 38/55 | (2006.01) |
| A61K 38/00 | (2006.01) |
| A61K 38/08 | (2006.01) |
| A61K 38/04 | (2006.01) |
| A61K 39/385 | (2006.01) |
| A61K 39/00 | (2006.01) |
| C07K 14/435 | (2006.01) |

(52) U.S. Cl.
CPC .......... *A61K 39/385* (2013.01); *A61K 39/0008* (2013.01); *A61K 2039/55505* (2013.01); *A61K 2039/6081* (2013.01); *A61K 2039/6037* (2013.01); *C07K 14/435* (2013.01)

(58) Field of Classification Search
None
See application file for complete search history.

(56) References Cited

U.S. PATENT DOCUMENTS

| 6,258,778 B1 * | 7/2001 | Rodgers et al. ............. 514/8.5 |
| 2006/0078554 A1 | 4/2006 | Bachmann |
| 2009/0175821 A1 | 7/2009 | Bridon et al. |

FOREIGN PATENT DOCUMENTS

| EP | 1548028 | 6/2005 |
| GB | 2 001 653 A | 2/1979 |
| WO | 96/40755 | 12/1996 |
| WO | WO 99/40107 A2 | 8/1999 |
| WO | WO 00/02905 A2 | 1/2000 |
| WO | 00/09144 A1 | 2/2000 |
| WO | WO 01/43761 A2 | 6/2001 |
| WO | WO 01/55176 A2 | 8/2001 |
| WO | WO 01/98325 A1 | 12/2001 |
| WO | WO 02/06308 A2 | 1/2002 |
| WO | WO 02/08284 A2 | 1/2002 |
| WO | WO 02/087504 A2 | 11/2002 |
| WO | 03/000720 | 1/2003 |
| WO | WO 03/031595 A2 | 4/2003 |
| WO | WO 2005/016962 A2 | 2/2005 |
| WO | WO 2005/044313 A2 | 5/2005 |
| WO | 2005/085430 A2 | 9/2005 |
| WO | WO 2009/023714 A2 | 2/2009 |

OTHER PUBLICATIONS

Gradman et al. 2008. Current Hypertension Reports 10:473-479.*
Campbell 2009. Current Hypertension Reports 11:63-68.*
Grote et al. 2004. Nephrol Dial Transplant 19:770-773.*
Verducchia et al. 2009. European Heart J. 30:679-688.*
Remuzzi et al. 2005. Kidney International 68 (suppl. 99):S57-S65.*
Benigni et al. 2010. EMBO Mol Med. 2:247-257.*
Maurer et al., Immunization against angiotensins for the treatment of hypertension, Clinical Immunology, 134: 89-95 (Jul. 2009).
Ambuehl et al., A vaccine for hypertension based on virus-like particles: preclinical efficacy and phase I safety and immunogenicity, Journal of Hypertension, 25: 63-72 (2007).
Brown et al., Randomized double-blind placebo-controlled study of an angiotensin immunotherapeutic vaccine (PMD3117) in hypertensive subjects, Clinical Science, 107: 167-173 (2004).
Downham et al., Evaluation of two carrier protein-angiotensin I conjugate vaccines to assess their future potential to control high blood pressure (hypertension) in man, British Journal of Clinical Pharmacology, 56: 505-512 (2003).

(Continued)

*Primary Examiner* — Shulamith H Shafer
(74) *Attorney, Agent, or Firm* — Nevrivy Patent Law Group P.L.L.C.

(57) ABSTRACT

Vaccine comprising a peptide bound to a pharmaceutically acceptable carrier, said peptide having the amino acid sequence (Formula I)                              (SEQ ID NO: 1)
$(X_1)_m (X_2)_n (X_3)_o X_4 X_5 HPX_6$, for treating and/or preventing a physical disorder associated with the renin-activated angiotensin system, wherein
$X_1$ is G or D,
$X_2$ is A, P, M, G, or R,
$X_3$ is G, A, H, or V,
$X_4$ is S, A, D, or Y,
$X_5$ is A, D, H, S, N, or I,
$X_6$ is A, L or F,
wherein m, n and o are independently 0 or 1 under the premise that when o is 0 m and n are 0 and when n is 0 m is 0, and wherein the peptide is not DRVYIHPF (SEQ ID NO:4).

9 Claims, 7 Drawing Sheets

(56) References Cited

OTHER PUBLICATIONS

Hagan et al., Recent advances in the discovery and delivery of vaccine adjuvants, Nature Reviews Drug Discovery, 2: 727-735 (2003).
Michel et al., Immunologic approaches to blockade of the renin-angiotensin system: A review, American Heart Journal, 117: 756-767 (1989).
Michel et al., Physiological and immunopathological consequences of active immunization of spontaneously hypertensive and normotensive rats against murine renin, Circulation, 81: 1899-1910 (1990).
Singh et al., Advances in vaccine adjuvants, Nature Biotechnology, 17: 1075-1081 (1999).
Soffer et al., Angiotensin-converting enzyme: immunologic, structural, and developmental aspects, Federation Proceedings, 42: 2735-2739 (1983).
Examination Report for Australian Patent Application No. 2010276069, mailed May 7, 2014.
Extended European Search Report for European Patent Application No. 13175730.4, mailed Mar. 24, 2014, Munich, Germany.
English language transaction of Japanese Offical Action for Japanese Patent Appl. No. 2012-520860, mailed Jan. 6, 2015, Japanese Patent Office.

* cited by examiner

SEQUENCE LISTING

```
<160> NUMBER OF SEQ ID NOS: 244

<210> SEQ ID NO 1
<211> LENGTH: 8
<212> TYPE: PRT
<213> ORGANISM: Artificial Sequence
<220> FEATURE:
<223> OTHER INFORMATION: Angiotensin II derived peptide
<220> FEATURE:
<221> NAME/KEY: MISC_FEATURE
<222> LOCATION: (1)..(1)
<223> OTHER INFORMATION: Xaa = (Xaa)m, wherein Xaa is G or D and m is 0
      or 1
<220> FEATURE:
```

```
<221> NAME/KEY: MISC_FEATURE
<222> LOCATION: (2)..(2)
<223> OTHER INFORMATION: Xaa = (Xaa)n, wherein Xaa is A, P, M, G or R
      and n is 0 or 1
<220> FEATURE:
<221> NAME/KEY: MISC_FEATURE
<222> LOCATION: (3)..(3)
<223> OTHER INFORMATION: Xaa = (Xaa)o, wherein Xaa is G, A, H or V and o
      is 0 or 1
<220> FEATURE:
<221> NAME/KEY: MISC_FEATURE
<222> LOCATION: (4)..(4)
<223> OTHER INFORMATION: Xaa is S, A, D or Y
<220> FEATURE:
<221> NAME/KEY: MISC_FEATURE
<222> LOCATION: (5)..(5)
<223> OTHER INFORMATION: Xaa is A, D, H, S, N or I
<220> FEATURE:
<221> NAME/KEY: MISC_FEATURE
<222> LOCATION: (6)..(6)
<223> OTHER INFORMATION: Xaa is A, L or F
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1

Xaa Xaa Xaa Xaa Xaa His Pro Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: Angiotensin II derived peptide
<220> FEATURE:
<221> NAME/KEY: MISC_FEATURE
<222> LOCATION: (1)..(1)
<223> OTHER INFORMATION: Xaa = (Xaa)m, wherein m is 0 or 1 and Xaa is G,
      A or D
<220> FEATURE:
<221> NAME/KEY: MISC_FEATURE
<222> LOCATION: (2)..(2)
<223> OTHER INFORMATION: Xaa = (Xaa)n, wherein n is 0 or 1 and Xaa is A,
      P, M, G or R
<220> FEATURE:
<221> NAME/KEY: MISC_FEATURE
<222> LOCATION: (3)..(3)
<223> OTHER INFORMATION: Xaa = (Xaa)o, wherein o is 0 or 1 and Xaa is G,
      A, H or V
<220> FEATURE:
<221> NAME/KEY: MISC_FEATURE
<222> LOCATION: (4)..(4)
<223> OTHER INFORMATION: Xaa is S, A, D or Y
<220> FEATURE:
<221> NAME/KEY: MISC_FEATURE
<222> LOCATION: (5)..(5)
<223> OTHER INFORMATION: Xaa is A, D, H, S, N or I
<220> FEATURE:
<221> NAME/KEY: MISC_FEATURE
<222> LOCATION: (6)..(6)
<223> OTHER INFORMATION: Xaa is Y or H
<220> FEATURE:
<221> NAME/KEY: MISC_FEATURE
<222> LOCATION: (8)..(8)
<223> OTHER INFORMATION: Xaa is A, V, L, I or F

<400> SEQUENCE: 2

Xaa Xaa Xaa Xaa Xaa Xaa Pro Xaa
1               5

<210> SEQ ID NO 3
<211> LENGTH: 8
<212> TYPE: PRT
```

```
<213> ORGANISM: Artificial Sequence
<220> FEATURE:
<223> OTHER INFORMATION: Angiotensin II derived peptide
<220> FEATURE:
<221> NAME/KEY: MISC_FEATURE
<222> LOCATION: (1)..(1)
<223> OTHER INFORMATION: Xaa is G, A or D
<220> FEATURE:
<221> NAME/KEY: MISC_FEATURE
<222> LOCATION: (2)..(2)
<223> OTHER INFORMATION: Xaa is A, P, M, G or R
<220> FEATURE:
<221> NAME/KEY: MISC_FEATURE
<222> LOCATION: (3)..(3)
<223> OTHER INFORMATION: Xaa is G, A, H or V
<220> FEATURE:
<221> NAME/KEY: MISC_FEATURE
<222> LOCATION: (4)..(4)
<223> OTHER INFORMATION: Xaa is S, A, D or Y
<220> FEATURE:
<221> NAME/KEY: MISC_FEATURE
<222> LOCATION: (5)..(5)
<223> OTHER INFORMATION: Xaa is A, D, H, S, N or I
<220> FEATURE:
<221> NAME/KEY: MISC_FEATURE
<222> LOCATION: (6)..(6)
<223> OTHER INFORMATION: Xaa is Y or H
<220> FEATURE:
<221> NAME/KEY: MISC_FEATURE
<222> LOCATION: (8)..(8)
<223> OTHER INFORMATION: Xaa is A, V, L, I or F

<400> SEQUENCE: 3

Xaa Xaa Xaa Xaa Xaa Xaa Pro Xaa
1               5

<210> SEQ ID NO 4
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 4

Asp Arg Val Tyr Ile His Pro Phe
1               5

<210> SEQ ID NO 5
<211> LENGTH: 10
<212> TYPE: PRT
<213> ORGANISM: Artificial Sequence
<220> FEATURE:
<223> OTHER INFORMATION: Angiotensin II derived peptide
<220> FEATURE:
<221> NAME/KEY: MISC_FEATURE
<222> LOCATION: (1)..(1)
<223> OTHER INFORMATION: Xaa is an amino acid residue selected from the
     group consisting of D, G, A, T, S, Q, E, K, R and H
<220> FEATURE:
<221> NAME/KEY: MISC_FEATURE
<222> LOCATION: (2)..(2)
<223> OTHER INFORMATION: Xaa is an amino acid residue selected from the
     group consisting of R, P, M, G, A, S, T, N, Q, D, E, K and H
<220> FEATURE:
<221> NAME/KEY: MISC_FEATURE
<222> LOCATION: (3)..(3)
<223> OTHER INFORMATION: Xaa is an amino acid residue selected from the
     group consisting of V, G, H, A, L, I, N, Q, D, E, K and R
<220> FEATURE:
<221> NAME/KEY: MISC_FEATURE
<222> LOCATION: (4)..(4)
<223> OTHER INFORMATION: Xaa is any amino acid residue
<220> FEATURE:
<221> NAME/KEY: MISC_FEATURE
<222> LOCATION: (5)..(5)
```

```
<223> OTHER INFORMATION: Xaa is an amino acid residue other than P, F, W
<220> FEATURE:
<221> NAME/KEY: MISC_FEATURE
<222> LOCATION: (6)..(6)
<223> OTHER INFORMATION: Xaa is an aromatic amino acid residue
<220> FEATURE:
<221> NAME/KEY: MISC_FEATURE
<222> LOCATION: (8)..(8)
<223> OTHER INFORMATION: Xaa is an amino acid residue selected from the
      group consisting of F, L, I, P, M, V, A, H, a non acidic amino
      acid residue and a non basic amino acid residue

<400> SEQUENCE: 5

Xaa Xaa Xaa Xaa Xaa Xaa Pro Xaa His Leu
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 6

Gly Arg Val Tyr Ile His Pro Phe
1               5

<210> SEQ ID NO 7
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 7

Asp Pro Val Tyr Ile His Pro Phe
1               5

<210> SEQ ID NO 8
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 8

Asp Met Val Tyr Ile His Pro Phe
1               5

<210> SEQ ID NO 9
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 9

Asp Gly Val Tyr Ile His Pro Phe
1               5

<210> SEQ ID NO 10
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 10
```

Asp Ala Val Tyr Ile His Pro Phe
1               5

<210> SEQ ID NO 11
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 11

Asp Arg Gly Tyr Ile His Pro Phe
1               5

<210> SEQ ID NO 12
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 12

Asp Arg Ala Tyr Ile His Pro Phe
1               5

<210> SEQ ID NO 13
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 13

Asp Arg His Tyr Ile His Pro Phe
1               5

<210> SEQ ID NO 14
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 14

Asp Arg Val Ala Ile His Pro Phe
1               5

<210> SEQ ID NO 15
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 15

Asp Arg Val Ser Ile His Pro Phe
1               5

<210> SEQ ID NO 16
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 16

Asp Arg Val Asp Ile His Pro Phe

<210> SEQ ID NO 17
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 17

Asp Arg Val Tyr Ala His Pro Phe
1               5

<210> SEQ ID NO 18
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 18

Asp Arg Val Tyr Asn His Pro Phe
1               5

<210> SEQ ID NO 19
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 19

Asp Arg Val Tyr Asp His Pro Phe
1               5

<210> SEQ ID NO 20
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 20

Asp Arg Val Tyr His His Pro Phe
1               5

<210> SEQ ID NO 21
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 21

Asp Arg Val Tyr Ser His Pro Phe
1               5

<210> SEQ ID NO 22
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 22

Asp Arg Val Tyr Ile Tyr Pro Phe
1               5

```
<210> SEQ ID NO 23
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 23

Asp Arg Val Tyr Ile His Pro Ala
1               5

<210> SEQ ID NO 24
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 24

Asp Arg Val Tyr Ile His Pro Val
1               5

<210> SEQ ID NO 25
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 25

Asp Arg Val Tyr Ile His Pro Leu
1               5

<210> SEQ ID NO 26
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 26

Asp Arg Val Tyr Ile His Pro Ile
1               5

<210> SEQ ID NO 27
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 27

Asp Ala Ala Tyr Ile His Pro Phe
1               5

<210> SEQ ID NO 28
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 28

Asp Arg Ala Ala Ile His Pro Phe
1               5
```

<210> SEQ ID NO 29
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 29

Asp Arg Val Ala Ala His Pro Phe
1               5

<210> SEQ ID NO 30
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 30

Asp Arg Ala Tyr Ala His Pro Phe
1               5

<210> SEQ ID NO 31
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 31

Asp Arg Ala Ala Ala His Pro Phe
1               5

<210> SEQ ID NO 32
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 32

Ala Arg Ala Ala Ile His Pro Phe
1               5

<210> SEQ ID NO 33
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 33

Ala Arg Val Ala Ala His Pro Phe
1               5

<210> SEQ ID NO 34
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 34

Asp Ala Ala Ala Ile His Pro Phe
1               5

```
<210> SEQ ID NO 35
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 35

Asp Ala Ala Ala Ala His Pro Phe
1               5

<210> SEQ ID NO 36
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 36

Asp Ala Val Ala Ala His Pro Phe
1               5

<210> SEQ ID NO 37
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 37

Asp Ala Gly Tyr Ile His Pro Phe
1               5

<210> SEQ ID NO 38
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 38

Asp Ala His Tyr Ile His Pro Phe
1               5

<210> SEQ ID NO 39
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 39

Asp Pro Gly Tyr Ile His Pro Phe
1               5

<210> SEQ ID NO 40
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 40

Asp Pro Ala Tyr Ile His Pro Phe
1               5

<210> SEQ ID NO 41
```

```
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 41

Asp Met Gly Tyr Ile His Pro Phe
1               5

<210> SEQ ID NO 42
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 42

Asp Met Ala Tyr Ile His Pro Phe
1               5

<210> SEQ ID NO 43
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 43

Asp Met His Tyr Ile His Pro Phe
1               5

<210> SEQ ID NO 44
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 44

Asp Gly Gly Tyr Ile His Pro Phe
1               5

<210> SEQ ID NO 45
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 45

Asp Gly Ala Tyr Ile His Pro Phe
1               5

<210> SEQ ID NO 46
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 46

Asp Gly His Tyr Ile His Pro Phe
1               5

<210> SEQ ID NO 47
<211> LENGTH: 8
```

```
<212> TYPE: PRT
<213> ORGANISM: Artificial Sequence
<220> FEATURE:
<223> OTHER INFORMATION: Angiotensin II derived peptide

<400> SEQUENCE: 47

Asp Pro Val Ala Ile His Pro Phe
1               5

<210> SEQ ID NO 48
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 48

Asp Pro Val Ser Ile His Pro Phe
1               5

<210> SEQ ID NO 49
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 49

Asp Met Val Ala Ile His Pro Phe
1               5

<210> SEQ ID NO 50
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 50

Asp Met Val Ser Ile His Pro Phe
1               5

<210> SEQ ID NO 51
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 51

Asp Arg Gly Ala Ile His Pro Phe
1               5

<210> SEQ ID NO 52
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 52

Asp Arg His Ala Ile His Pro Phe
1               5

<210> SEQ ID NO 53
<211> LENGTH: 8
<212> TYPE: PRT
```

```
<213> ORGANISM: Artificial Sequence
<220> FEATURE:
<223> OTHER INFORMATION: Angiotensin II derived peptide

<400> SEQUENCE: 53

Asp Arg Gly Tyr Ala His Pro Phe
1               5

<210> SEQ ID NO 54
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 54

Asp Arg Gly Tyr Asp His Pro Phe
1               5

<210> SEQ ID NO 55
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 55

Asp Arg Gly Tyr His His Pro Phe
1               5

<210> SEQ ID NO 56
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 56

Asp Arg Gly Tyr Ser His Pro Phe
1               5

<210> SEQ ID NO 57
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 57

Asp Arg Gly Tyr Asn His Pro Phe
1               5

<210> SEQ ID NO 58
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 58

Asp Arg Ala Tyr Asp His Pro Phe
1               5

<210> SEQ ID NO 59
<211> LENGTH: 8
<212> TYPE: PRT
<213> ORGANISM: Artificial Sequence
```

```
<220> FEATURE:
<223> OTHER INFORMATION: Angiotensin II derived peptide

<400> SEQUENCE: 59

Asp Arg Ala Tyr His His Pro Phe
1               5

<210> SEQ ID NO 60
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 60

Asp Arg Ala Tyr Ser His Pro Phe
1               5

<210> SEQ ID NO 61
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 61

Asp Arg Ala Tyr Asn His Pro Phe
1               5

<210> SEQ ID NO 62
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 62

Asp Arg His Tyr Ala His Pro Phe
1               5

<210> SEQ ID NO 63
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 63

Asp Arg His Tyr Ser His Pro Phe
1               5

<210> SEQ ID NO 64
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 64

Asp Arg His Tyr Asn His Pro Phe
1               5

<210> SEQ ID NO 65
<211> LENGTH: 8
<212> TYPE: PRT
<213> ORGANISM: Artificial Sequence
<220> FEATURE:
```

<223> OTHER INFORMATION: Angiotensin II derived peptide

<400> SEQUENCE: 65

Asp Arg His Tyr Asp His Pro Phe
1               5

<210> SEQ ID NO 66
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 66

Asp Arg His Tyr His His Pro Phe
1               5

<210> SEQ ID NO 67
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 67

Asp Arg His Tyr Ile Tyr Pro Phe
1               5

<210> SEQ ID NO 68
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 68

Asp Arg Gly Ala Asp His Pro Phe
1               5

<210> SEQ ID NO 69
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 69

Asp Arg Gly Ala His His Pro Phe
1               5

<210> SEQ ID NO 70
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 70

Asp Arg Val Ala His His Pro Phe
1               5

<210> SEQ ID NO 71
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 71

Asp Arg His Ala Asp His Pro Phe
1               5

<210> SEQ ID NO 72
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 72

Gly Arg Gly Ala Ile His Pro Phe
1               5

<210> SEQ ID NO 73
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 73

Gly Arg His Ser Ile His Pro Phe
1               5

<210> SEQ ID NO 74
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 74

Gly Arg His Ala Asp Tyr Pro Phe
1               5

<210> SEQ ID NO 75
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 75

Asp Pro Gly Ala Ile His Pro Phe
1               5

<210> SEQ ID NO 76
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 76

Gly Arg His Ala Ile His Pro Phe
1               5

<210> SEQ ID NO 77
<211> LENGTH: 8
<212> TYPE: PRT
<213> ORGANISM: Artificial Sequence
<220> FEATURE:
<223> OTHER INFORMATION: Angiotensin II derived peptide

```
<400> SEQUENCE: 77

Asp Pro Gly Ser Ile His Pro Phe
1               5

<210> SEQ ID NO 78
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 78

Asp Met Gly Ala Ile His Pro Phe
1               5

<210> SEQ ID NO 79
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 79

Asp Met Gly Ser Ile His Pro Phe
1               5

<210> SEQ ID NO 80
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 80

Gly Pro Gly Tyr Ile His Pro Phe
1               5

<210> SEQ ID NO 81
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 81

Gly Met Gly Tyr Ile His Pro Phe
1               5

<210> SEQ ID NO 82
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 82

Gly Pro Gly Ser Ile His Pro Phe
1               5

<210> SEQ ID NO 83
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 83
```

```
Gly Met Gly Ser Ile His Pro Phe
1               5

<210> SEQ ID NO 84
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 84

Asp Arg Gly Ser Ile His Pro Phe
1               5

<210> SEQ ID NO 85
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 85

Asp Pro His Ala Ile His Pro Phe
1               5

<210> SEQ ID NO 86
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 86

Asp Met His Ala Ile His Pro Phe
1               5

<210> SEQ ID NO 87
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 87

Gly Pro His Ala Ile His Pro Phe
1               5

<210> SEQ ID NO 88
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 88

Gly Met His Ala Ile His Pro Phe
1               5

<210> SEQ ID NO 89
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 89
```

```
Gly Pro His Ser Ile His Pro Phe
1               5

<210> SEQ ID NO 90
<211> LENGTH: 8
<212> TYPE: PRT
<213> ORGANISM: Artificial Sequence
<220> FEATURE:
<223> OTHER INFORMATION: Angiotensin II derived peptide

<400> SEQUENCE: 90

Gly Met His Ser Ile His Pro Phe
1               5

<210> SEQ ID NO 91
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 91

Pro Val Tyr Ile His Pro Phe
1               5

<210> SEQ ID NO 92
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 92

Met Val Tyr Ile His Pro Phe
1               5

<210> SEQ ID NO 93
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 93

Gly Val Tyr Ile His Pro Phe
1               5

<210> SEQ ID NO 94
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 94

Ala Val Tyr Ile His Pro Phe
1               5

<210> SEQ ID NO 95
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 95

Arg Gly Tyr Ile His Pro Phe
```

```
<210> SEQ ID NO 96
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 96

Arg Ala Tyr Ile His Pro Phe
1               5

<210> SEQ ID NO 97
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 97

Arg His Tyr Ile His Pro Phe
1               5

<210> SEQ ID NO 98
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 98

Arg Val Ala Ile His Pro Phe
1               5

<210> SEQ ID NO 99
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 99

Arg Val Ser Ile His Pro Phe
1               5

<210> SEQ ID NO 100
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 100

Arg Val Asp Ile His Pro Phe
1               5

<210> SEQ ID NO 101
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 101

Arg Val Tyr Ala His Pro Phe
1               5
```

<210> SEQ ID NO 102
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 102

Arg Val Tyr Asn His Pro Phe
1               5

<210> SEQ ID NO 103
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 103

Arg Val Tyr Asp His Pro Phe
1               5

<210> SEQ ID NO 104
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 104

Arg Val Tyr His His Pro Phe
1               5

<210> SEQ ID NO 105
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 105

Arg Val Tyr Ser His Pro Phe
1               5

<210> SEQ ID NO 106
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 106

Arg Val Tyr Ile Tyr Pro Phe
1               5

<210> SEQ ID NO 107
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 107

Arg Val Tyr Ile His Pro Ala
1               5

<210> SEQ ID NO 108
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 108

Arg Val Tyr Ile His Pro Val
1               5

<210> SEQ ID NO 109
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 109

Arg Val Tyr Ile His Pro Leu
1               5

<210> SEQ ID NO 110
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 110

Arg Val Tyr Ile His Pro Ile
1               5

<210> SEQ ID NO 111
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 111

Ala Ala Tyr Ile His Pro Phe
1               5

<210> SEQ ID NO 112
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 112

Arg Ala Ala Ile His Pro Phe
1               5

<210> SEQ ID NO 113
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 113

Arg Val Ala Ala His Pro Phe
1               5

```
<210> SEQ ID NO 114
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 114

Arg Ala Tyr Ala His Pro Phe
1               5

<210> SEQ ID NO 115
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 115

Arg Ala Ala Ala His Pro Phe
1               5

<210> SEQ ID NO 116
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 116

Arg Ala Ala Ile His Pro Phe
1               5

<210> SEQ ID NO 117
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 117

Arg Val Ala Ala His Pro Phe
1               5

<210> SEQ ID NO 118
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 118

Ala Ala Ala Ile His Pro Phe
1               5

<210> SEQ ID NO 119
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 119

Ala Ala Ala Ala His Pro Phe
1               5

<210> SEQ ID NO 120
```

```
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 120

Ala Val Ala Ala His Pro Phe
1               5

<210> SEQ ID NO 121
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 121

Ala Gly Tyr Ile His Pro Phe
1               5

<210> SEQ ID NO 122
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 122

Ala His Tyr Ile His Pro Phe
1               5

<210> SEQ ID NO 123
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 123

Pro Gly Tyr Ile His Pro Phe
1               5

<210> SEQ ID NO 124
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 124

Pro Ala Tyr Ile His Pro Phe
1               5

<210> SEQ ID NO 125
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 125

Met Gly Tyr Ile His Pro Phe
1               5

<210> SEQ ID NO 126
<211> LENGTH: 7
```

```
<212> TYPE: PRT
<213> ORGANISM: Artificial Sequence
<220> FEATURE:
<223> OTHER INFORMATION: Angiotensin II derived peptide

<400> SEQUENCE: 126

Met Ala Tyr Ile His Pro Phe
1               5

<210> SEQ ID NO 127
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 127

Met His Tyr Ile His Pro Phe
1               5

<210> SEQ ID NO 128
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 128

Gly Gly Tyr Ile His Pro Phe
1               5

<210> SEQ ID NO 129
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 129

Gly Ala Tyr Ile His Pro Phe
1               5

<210> SEQ ID NO 130
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 130

Gly His Tyr Ile His Pro Phe
1               5

<210> SEQ ID NO 131
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 131

Pro Val Ala Ile His Pro Phe
1               5

<210> SEQ ID NO 132
<211> LENGTH: 7
<212> TYPE: PRT
```

<213> ORGANISM: Artificial Sequence
<220> FEATURE:
<223> OTHER INFORMATION: Angiotensin II derived peptide

<400> SEQUENCE: 132

Pro Val Ser Ile His Pro Phe
1               5

<210> SEQ ID NO 133
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 133

Met Val Ala Ile His Pro Phe
1               5

<210> SEQ ID NO 134
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 134

Met Val Ser Ile His Pro Phe
1               5

<210> SEQ ID NO 135
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 135

Arg Gly Ala Ile His Pro Phe
1               5

<210> SEQ ID NO 136
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 136

Arg His Ala Ile His Pro Phe
1               5

<210> SEQ ID NO 137
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 137

Arg Gly Tyr Ala His Pro Phe
1               5

<210> SEQ ID NO 138
<211> LENGTH: 7
<212> TYPE: PRT
<213> ORGANISM: Artificial Sequence

```
<220> FEATURE:
<223> OTHER INFORMATION: Angiotensin II derived peptide

<400> SEQUENCE: 138

Arg Gly Tyr Asp His Pro Phe
1               5

<210> SEQ ID NO 139
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 139

Arg Gly Tyr His His Pro Phe
1               5

<210> SEQ ID NO 140
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 140

Arg Gly Tyr Ser His Pro Phe
1               5

<210> SEQ ID NO 141
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 141

Arg Gly Tyr Asn His Pro Phe
1               5

<210> SEQ ID NO 142
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 142

Arg Ala Tyr Asp His Pro Phe
1               5

<210> SEQ ID NO 143
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 143

Arg Ala Tyr His His Pro Phe
1               5

<210> SEQ ID NO 144
<211> LENGTH: 7
<212> TYPE: PRT
<213> ORGANISM: Artificial Sequence
<220> FEATURE:
```

<223> OTHER INFORMATION: Angiotensin II derived peptide

<400> SEQUENCE: 144

Arg Ala Tyr Ser His Pro Phe
1               5

<210> SEQ ID NO 145
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 145

Arg Ala Tyr Asn His Pro Phe
1               5

<210> SEQ ID NO 146
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 146

Arg His Tyr Ala His Pro Phe
1               5

<210> SEQ ID NO 147
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 147

Arg His Tyr Ser His Pro Phe
1               5

<210> SEQ ID NO 148
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 148

Arg His Tyr Asn His Pro Phe
1               5

<210> SEQ ID NO 149
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 149

Arg His Tyr Asp His Pro Phe
1               5

<210> SEQ ID NO 150
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 150

Arg His Tyr His His Pro Phe
1               5

<210> SEQ ID NO 151
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 151

Arg His Tyr Ile Tyr Pro Phe
1               5

<210> SEQ ID NO 152
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 152

Arg Gly Ala Asp His Pro Phe
1               5

<210> SEQ ID NO 153
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 153

Arg Gly Ala His His Pro Phe
1               5

<210> SEQ ID NO 154
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 154

Arg Val Ala His His Pro Phe
1               5

<210> SEQ ID NO 155
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 155

Arg His Ala Asp His Pro Phe
1               5

<210> SEQ ID NO 156
<211> LENGTH: 7
<212> TYPE: PRT
<213> ORGANISM: Artificial Sequence
<220> FEATURE:
<223> OTHER INFORMATION: Angiotensin II derived peptide

```
<400> SEQUENCE: 156

Arg Gly Ala Ile His Pro Phe
1               5

<210> SEQ ID NO 157
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 157

Arg His Ser Ile His Pro Phe
1               5

<210> SEQ ID NO 158
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 158

Arg His Ala Asp Tyr Pro Phe
1               5

<210> SEQ ID NO 159
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 159

Pro Gly Ala Ile His Pro Phe
1               5

<210> SEQ ID NO 160
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 160

Arg His Ala Ile His Pro Phe
1               5

<210> SEQ ID NO 161
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 161

Pro Gly Ser Ile His Pro Phe
1               5

<210> SEQ ID NO 162
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 162
```

```
Met Gly Ala Ile His Pro Phe
1               5

<210> SEQ ID NO 163
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 163

Met Gly Ser Ile His Pro Phe
1               5

<210> SEQ ID NO 164
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 164

Pro Gly Tyr Ile His Pro Phe
1               5

<210> SEQ ID NO 165
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 165

Met Gly Tyr Ile His Pro Phe
1               5

<210> SEQ ID NO 166
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 166

Arg Gly Ser Ile His Pro Phe
1               5

<210> SEQ ID NO 167
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 167

Pro His Ala Ile His Pro Phe
1               5

<210> SEQ ID NO 168
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 168
```

```
Met His Ala Ile His Pro Phe
1               5
```

<210> SEQ ID NO 169
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 169

```
Pro His Ser Ile His Pro Phe
1               5
```

<210> SEQ ID NO 170
<211> LENGTH: 7
<212> TYPE: PRT
<213> ORGANISM: Artificial Sequence
<220> FEATURE:
<223> OTHER INFORMATION: Angiotensin II derived peptide

<400> SEQUENCE: 170

```
Met His Ser Ile His Pro Phe
1               5
```

<210> SEQ ID NO 171
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 171

```
Gly Tyr Ile His Pro Phe
1               5
```

<210> SEQ ID NO 172
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 172

```
Ala Tyr Ile His Pro Phe
1               5
```

<210> SEQ ID NO 173
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 173

```
His Tyr Ile His Pro Phe
1               5
```

<210> SEQ ID NO 174
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 174

```
Val Ala Ile His Pro Phe
```

```
1               5
```

<210> SEQ ID NO 175
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 175

```
Val Asp Ile His Pro Phe
1               5
```

<210> SEQ ID NO 176
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 176

```
Val Tyr Ala His Pro Phe
1               5
```

<210> SEQ ID NO 177
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 177

```
Val Tyr Asn His Pro Phe
1               5
```

<210> SEQ ID NO 178
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 178

```
Val Tyr Asp His Pro Phe
1               5
```

<210> SEQ ID NO 179
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 179

```
Val Tyr His His Pro Phe
1               5
```

<210> SEQ ID NO 180
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 180

```
Val Tyr Ser His Pro Phe
1               5
```

```
<210> SEQ ID NO 181
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 181

Val Tyr Ile Tyr Pro Phe
1               5

<210> SEQ ID NO 182
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 182

Val Tyr Ile His Pro Ala
1               5

<210> SEQ ID NO 183
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 183

Val Tyr Ile His Pro Val
1               5

<210> SEQ ID NO 184
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 184

Val Tyr Ile His Pro Leu
1               5

<210> SEQ ID NO 185
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 185

Val Tyr Ile His Pro Ile
1               5

<210> SEQ ID NO 186
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 186

Ala Ala Ile His Pro Phe
1               5
```

```
<210> SEQ ID NO 187
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 187

Val Ala Ala His Pro Phe
1               5

<210> SEQ ID NO 188
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 188

Ala Tyr Ala His Pro Phe
1               5

<210> SEQ ID NO 189
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 189

Ala Ala Ala His Pro Phe
1               5

<210> SEQ ID NO 190
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 190

His Tyr Ile His Pro Phe
1               5

<210> SEQ ID NO 191
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 191

Val Ser Ile His Pro Phe
1               5

<210> SEQ ID NO 192
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 192

Gly Ala Ile His Pro Phe
1               5
```

```
<210> SEQ ID NO 193
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 193

His Ala Ile His Pro Phe
1               5

<210> SEQ ID NO 194
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 194

Gly Tyr Ala His Pro Phe
1               5

<210> SEQ ID NO 195
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 195

Gly Tyr Asp His Pro Phe
1               5

<210> SEQ ID NO 196
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 196

Gly Tyr His His Pro Phe
1               5

<210> SEQ ID NO 197
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 197

Gly Tyr Ser His Pro Phe
1               5

<210> SEQ ID NO 198
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 198

Gly Tyr Asn His Pro Phe
1               5

<210> SEQ ID NO 199
```

```
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 199

Ala Tyr Asp His Pro Phe
1               5

<210> SEQ ID NO 200
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 200

Ala Tyr His His Pro Phe
1               5

<210> SEQ ID NO 201
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 201

Ala Tyr Ser His Pro Phe
1               5

<210> SEQ ID NO 202
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 202

Ala Tyr Asn His Pro Phe
1               5

<210> SEQ ID NO 203
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 203

His Tyr Ala His Pro Phe
1               5

<210> SEQ ID NO 204
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 204

His Tyr Ser His Pro Phe
1               5

<210> SEQ ID NO 205
<211> LENGTH: 6
```

<212> TYPE: PRT
<213> ORGANISM: Artificial Sequence
<220> FEATURE:
<223> OTHER INFORMATION: Angiotensin II derived peptide

<400> SEQUENCE: 205

His Tyr Asn His Pro Phe
1               5

<210> SEQ ID NO 206
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 206

His Tyr Asp His Pro Phe
1               5

<210> SEQ ID NO 207
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 207

His Tyr His His Pro Phe
1               5

<210> SEQ ID NO 208
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 208

His Tyr Ile Tyr Pro Phe
1               5

<210> SEQ ID NO 209
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 209

Gly Ala Asp His Pro Phe
1               5

<210> SEQ ID NO 210
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 210

Gly Ala His His Pro Phe
1               5

<210> SEQ ID NO 211
<211> LENGTH: 6
<212> TYPE: PRT

```
<213> ORGANISM: Artificial Sequence
<220> FEATURE:
<223> OTHER INFORMATION: Angiotensin II derived peptide

<400> SEQUENCE: 211

Val Ala His His Pro Phe
1               5

<210> SEQ ID NO 212
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 212

His Ala Asp His Pro Phe
1               5

<210> SEQ ID NO 213
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 213

Gly Ala Ile His Pro Phe
1               5

<210> SEQ ID NO 214
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 214

His Ser Ile His Pro Phe
1               5

<210> SEQ ID NO 215
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 215

His Ala Asp Tyr Pro Phe
1               5

<210> SEQ ID NO 216
<211> LENGTH: 6
<212> TYPE: PRT
<213> ORGANISM: Artificial Sequence
<220> FEATURE:
<223> OTHER INFORMATION: Angiotensin II derived peptide

<400> SEQUENCE: 216

Gly Ser Ile His Pro Phe
1               5

<210> SEQ ID NO 217
<211> LENGTH: 6
<212> TYPE: PRT
<213> ORGANISM: Artificial Sequence
```

```
<220> FEATURE:
<223> OTHER INFORMATION: Angiotensin II derived peptide

<400> SEQUENCE: 217

His Ala Ile His Pro Phe
1               5

<210> SEQ ID NO 218
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 218

Ala Ile His Pro Phe
1               5

<210> SEQ ID NO 219
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 219

Ser Ile His Pro Phe
1               5

<210> SEQ ID NO 220
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 220

Asp Ile His Pro Phe
1               5

<210> SEQ ID NO 221
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 221

Tyr Ala His Pro Phe
1               5

<210> SEQ ID NO 222
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 222

Tyr Asn His Pro Phe
1               5

<210> SEQ ID NO 223
<211> LENGTH: 5
<212> TYPE: PRT
<213> ORGANISM: Artificial Sequence
<220> FEATURE:
```

<223> OTHER INFORMATION: Angiotensin II derived peptide

<400> SEQUENCE: 223

Tyr Asp His Pro Phe
1               5

<210> SEQ ID NO 224
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 224

Tyr His His Pro Phe
1               5

<210> SEQ ID NO 225
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 225

Tyr Ser His Pro Phe
1               5

<210> SEQ ID NO 226
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 226

Tyr Ile Tyr Pro Phe
1               5

<210> SEQ ID NO 227
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 227

Tyr Ile His Pro Ala
1               5

<210> SEQ ID NO 228
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 228

Tyr Ile His Pro Val
1               5

<210> SEQ ID NO 229
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 229

Tyr Ile His Pro Leu
1               5

<210> SEQ ID NO 230
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 230

Tyr Ile His Pro Ile
1               5

<210> SEQ ID NO 231
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 231

Ala Ala His Pro Phe
1               5

<210> SEQ ID NO 232
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 232

Ala Asp His Pro Phe
1               5

<210> SEQ ID NO 233
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 233

Ala His His Pro Phe
1               5

<210> SEQ ID NO 234
<211> LENGTH: 5
<212> TYPE: PRT
<213> ORGANISM: Artificial Sequence
<220> FEATURE:
<223> OTHER INFORMATION: Angiotensin II derived peptide

<400> SEQUENCE: 234

Ala Asp Tyr Pro Phe
1               5

<210> SEQ ID NO 235
<211> LENGTH: 9
<212> TYPE: PRT
<213> ORGANISM: Artificial Sequence
<220> FEATURE:
<223> OTHER INFORMATION: Angiotensin II derived peptide

```
<400> SEQUENCE: 235

Cys Asp Arg Val Tyr Ile His Pro Phe
1               5

<210> SEQ ID NO 236
<211> LENGTH: 9
<212> TYPE: PRT
<213> ORGANISM: Artificial Sequence
<220> FEATURE:
<223> OTHER INFORMATION: Angiotensin II derived peptide

<400> SEQUENCE: 236

Cys Asp Ala Val Tyr Ile His Pro Phe
1               5

<210> SEQ ID NO 237
<211> LENGTH: 9
<212> TYPE: PRT
<213> ORGANISM: Artificial Sequence
<220> FEATURE:
<223> OTHER INFORMATION: Angiotensin II derived peptide

<400> SEQUENCE: 237

Cys Asp Glu Val Tyr Ile His Pro Phe
1               5

<210> SEQ ID NO 238
<211> LENGTH: 9
<212> TYPE: PRT
<213> ORGANISM: Artificial Sequence
<220> FEATURE:
<223> OTHER INFORMATION: Angiotensin II derived peptide

<400> SEQUENCE: 238

Cys Asp Phe Val Tyr Ile His Pro Phe
1               5

<210> SEQ ID NO 239
<211> LENGTH: 9
<212> TYPE: PRT
<213> ORGANISM: Artificial Sequence
<220> FEATURE:
<223> OTHER INFORMATION: Angiotensin II derived peptide

<400> SEQUENCE: 239

Cys Asp His Val Tyr Ile His Pro Phe
1               5

<210> SEQ ID NO 240
<211> LENGTH: 9
<212> TYPE: PRT
<213> ORGANISM: Artificial Sequence
<220> FEATURE:
<223> OTHER INFORMATION: Angiotensin II derived peptide

<400> SEQUENCE: 240

Cys Asp Lys Val Tyr Ile His Pro Phe
1               5

<210> SEQ ID NO 241
<211> LENGTH: 9
<212> TYPE: PRT
<213> ORGANISM: Artificial Sequence
<220> FEATURE:
<223> OTHER INFORMATION: Angiotensin II derived peptide

<400> SEQUENCE: 241
```

```
Cys Asp Met Val Tyr Ile His Pro Phe
1               5

<210> SEQ ID NO 242
<211> LENGTH: 9
<212> TYPE: PRT
<213> ORGANISM: Artificial Sequence
<220> FEATURE:
<223> OTHER INFORMATION: Angiotensin II derived peptide

<400> SEQUENCE: 242

Cys Asp Val Val Tyr Ile His Pro Phe
1               5

<210> SEQ ID NO 243
<211> LENGTH: 9
<212> TYPE: PRT
<213> ORGANISM: Artificial Sequence
<220> FEATURE:
<223> OTHER INFORMATION: Angiotensin II derived peptide

<400> SEQUENCE: 243

Cys Asp Tyr Val Tyr Ile His Pro Phe
1               5

<210> SEQ ID NO 244
<211> LENGTH: 9
<212> TYPE: PRT
<213> ORGANISM: Artificial Sequence
<220> FEATURE:
<223> OTHER INFORMATION: Angiotensin II derived peptide

<400> SEQUENCE: 244

Cys Asp Pro Val Tyr Ile His Pro Phe
1               5
```

VACCINE

CROSS-REFERENCE TO RELATED APPLICATIONS

Not Applicable.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

REFERENCE TO A SEQUENCE LISTING SUBMITTED ELECTRONICALLY VIA EFS-WEB

The content of the sequence listing (Name: seq listing ST25.txt, Size: 49,617 bytes; and Date of Creation: Apr. 6, 2012) electronically submitted via EFS-Web is incorporated by reference in its entirety.

BACKGROUND OF THE INVENTION

1. Field of the Invention

The present invention relates to a medicament to be used in the fields of medicine, immunology, molecular biology and virology preferentially to prevent and/or treat physical disorders associated with the renin-activated angiotensin system, preferably hypertension and hypertension-associated cardiovascular diseases (CVD).

2. Description of Related Art

The renin angiotensin system (RAS), also known as renin angiotensin aldosteron system (RAAS), is a hormone system that regulates different physiological processes in the body. RAS activity is initiated by the cleavage of the peptide angiotensinogen to the decapeptide angiotensin I (Ang I) by the enzyme renin. The key product of the renin system is the octapeptide hormone angiotensin II (Ang II), which is formed from Ang I by the angiotensin-converting enzyme (ACE). RAS plays a key role in volume regulation and the maintenance of blood pressure. However, excessive activity of the renin system is associated with hypertension and target organ damage.

In recent years it became clear that the renin angiotensin system (RAS) extends well beyond their classical role in blood pressure regulation and salt-water balance. Beside regulating the physiological and pathophysiological processes of cardiovascular and renin tissue, the RAS has been described to act on a number of additional tissues, including, brain, endocrine, sensory, fat and immune cells. Thus the RAS plays an important role in physiological and pathophysiological processes of these tissues as well.

Since physiological and pathophysiological implications of the RAS are extremely broad medications targeting the RAS have become key clinical tools in the treatment of cardiovascular and renal diseases, such as hypertension, heart failure and diabetic nephropthy. Moreover different studies show that blocking the RAS does not only influence cardiovascular diseases connected to high blood pressure but can also reduce cardiovascular events linked to inflammatory processes such as atherosclerosis. These basic research and animal studies strongly support angiotensin II as a proinflammatory mediator, which directly induces atherosclerotic plaque development and heart remodeling.

In addition, RAS seems to be central not only to the inflammatory aspects of atherosclerosis but also of autoimmune diseases such as multiple sclerosis.

Furthermore, evidence suggests that blockade of the renin-angiotensin system decreases the occurrence of new-onset diabetes and reduces the risk of diabetic complications. Other studies provide an overview of the effects of Ang II leading to the development of insulin resistance and its implications for diabetes. Components of the renin-angiotensin system have a complex interaction with insulin action and the development and progression of metabolic diseases.

RAS, Inflammatory Disorders and Autoimmune Disorders (Atherosclerosis and Multiple Sclerosis)

Atherosclerosis is a chronic inflammatory disease, which involves vascular cells, immune system, and several organs. Although leukocytes, endothelial and smooth muscle cells have been shown to play a crucial role in atherosclerotic inflammation, recent evidence also supports a direct activity for cytokines and chemokines, factors that have been shown to modulate inflammatory processes. Recent studies now suggest new inflammatory activities for the peptide hormone angiotensin II. The renin-angiotensin system serves an important role in promoting inflammation, since angiotensin II induces proatherosclerotic cytokine secretion and increases endothelial dysfunction. Angiotensin II regulates not only cytokine, chemokine, and growth factor secretion within the arterial wall but regulates also the expression of adhesion molecules (VCAM-1, ICAM-1, P-selectin). Beside this it has been shown that the renin-angiotensin system can modulate the activation of complement system in both atherosclerosis and renal injury. This inflammatory cascade activates the vascular inflammatory response by increasing inflammatory cell recruitment to intima. Recruited cells can produce angiotensin II, resulting in a positive feedback response, which can maintain this inflammatory vicious circle.

Recently different publications show that the intersection between chronic inflammatory diseases like multiple sclerosis (MS) and the most common of all of the human chronic diseases, atherosclerosis, may go far beyond the root "sclerosis", which is shared in both their names. They showed that the RAS also plays a major role in autoimmunity, exemplified by multiple sclerosis (MS) and its animal model, experimental autoimmune encephalomyelitis (EAE). Using proteomics, the authors observed that RAS is up-regulated in brain lesions of MS. Blocking angiotensin II production with ACE inhibitors or inhibiting angiotensin II signaling with angiotensin II receptor blockers suppressed autoreactive TH1 and TH17 cells and promoted antigen-specific CD4_FoxP3_regulatory T cells (Treg cells). Treatment with ACE inhibitors induces abundant CD4_FoxP3_T cells with sufficient potency to reverse paralytic EAE. Therefore, authors concluded that modulation of the RAS is an attractive therapeutic strategy for application to human autoimmune diseases.

RAS and Cardiovascular Diseases—Hypertension

Cardiovascular disease (CVD) is the leading cause of death throughout the world. According to the World Health Organization (WHO) approximately 30% of all global deaths can be attributed to CVD. CVD is caused by disorders of the heart and blood vessels and encompasses various manifestations. These include myocardial infarction, stroke, heart failure, and end stage renal disease. The most prevalent risk factor for CVD is hypertension. More than a quarter of the world's adult population had hypertension in 2000 and if appropriate action is not taken, this numbers will increase continuously.

Hypertension, commonly referred to as high blood pressure is defined as chronically elevated blood pressure with a systolic blood pressure above 140 mmHg and/or a diastolic blood pressure above 90 mmHg. Guidelines defined by the "Joint National Committee on Prevention, Detection, Evaluation, and Treatment of High Blood Pressure" suggest that persons with a blood pressure between 120 and 139 mmHg systolic and/or a blood pressure between 80 and 89 mmHg diastolic should be considered pre-hypertensive and require health-promoting changes to prevent CVD. Therefore, lowering the blood pressure is an important strategy to prevent CVD. As first step, blood pressure reduction can be achieved by changes in life style targeting the primary factors like unhealthy diet, physical inactivity, and smoking. However, treatment of essential hypertension requires specific therapies. A key regulator of the blood pressure is the renin-angiotensin system (RAS) which has become an attractive target for therapeutic intervention. Therefore pharmaceuticals that specifically act on components of the RAS have become important clinical tools in the treatment of hypertension.

The RAS pathway is a cascade beginning with the cleavage of angiotensinogen by renin. Renin is an aspartyl protease synthesized and stored primarily in the granules of juxtaglomerular cells in the kidney and has high substrate specificity for angiotensinogen. Angiotensinogen is mainly formed and constitutively secreted into the circulation by hepatic cells. It is cleaved at the N-terminus by renin to form the decapeptide Angiotensin I (Ang I; the 1-10 peptide) which is rapidly converted into the biological active octapeptide angiotensin II (Ang II; the 1-8 peptide). In contrast to Ang II, Ang I appears to have no biological activity and exists solely as a precursor for Ang II. Cleavage of Ang I is mediated basically, but not exclusively by the angiotensin-converting enzyme (ACE). This membrane-bound metalloproteinase is expressed on the surface of endothelial cells with the highest concentrations found on the vascular epithelium in the lung. Besides ACE chymase has been shown to produce Ang II. Ang II can also directly be generated from angiotensinogen by enzymes like tonin and cathepsin. In addition, other Ang I- and Ang II-derived, functional peptides can be found in the circulation. These are generated by amino-, carboxy- or endopeptidases and include Ang(1-9), Ang(1-7), Ang III (the 2-8 peptide) and Ang IV (the 3-8 peptide). A carboxypeptidase, known as angiotensin-converting enzyme II (ACE2), acts on Ang I as well as Ang II. ACE2 generates Ang1-9 from Ang I and Ang1-7 from Ang II. Ang1-9 can then be further converted to Ang1-7 by ACE. In contrast to Ang II, which elevates blood pressure and appears to be the major mediator of vascular remodeling in hypertension, Ang1-7 peptide promotes vasodilation and by that may counteract the potentially detrimental actions of Ang II. The peptide Ang1-7 acts via its receptor the mas oncogen product (MAS).

Ang II and Ang 1-7 are considered as the main effector peptides of the RAS, while Ang III and Ang IV have some lesser activity (approximately 40% of the activity of Ang II). The actions of Ang II are mediated predominantly by two seven transmembrane receptors termed Ang II receptors, type 1 (AT1; subtypes 1a and 1b) and type 2 (AT2). The AT1 and AT2 subtypes bind Ang II similarly, but have a different cellular localization and are differentially expressed in diverse tissues. Most of the Ang II hypertensinogenic actions are attributed to the AT1 receptor.

Throughout the body Ang II is a potent vasoconstrictor. In the kidneys it constricts glomerular arterioles thereby increasing systemic arterial blood pressure and decreasing blood flow. In the adrenal cortex, it causes the release of aldosterone which in turn causes the tubules in the kidneys to reabsorb more sodium and water from the urine. It also acts on the central nervous system to increase a person's appetite for salt and to make them feel thirsty. Additionally, Ang II stimulates the release of Anti Diuretic Hormone (ADH).

The classical role of components of the RAS is to act as endocrine factors in order to maintain blood pressure and electrolyte as well as fluid balance. In addition to this circulating RAS a local angiotensin-generating cascade exists in several tissues. The so-called tissue RAS can act locally as a paracrine and/or autocrine factor and can operate, in whole or in part, independently of the circulating counterpart.

Currently several drugs are on the market to treat hypertension. These encompass for example diuretics and calcium-channel blockers and include numerous pharmaceuticals that specifically target components of the RAS. The latter include ACE inhibitors which act by binding to the active side of ACE and interfering with the ability of the enzyme to bind and cleave its substrates. Characteristic side effects of ACE inhibitors are dry cough and first dose hypotension/angioneurotic oedema. Another class of pharmaceuticals that target the RAS is angiotensin receptor (AT1) blockers (ARBs). ARBs specifically interfere with the function of Ang II by blocking the binding of angiotensin II to the AT1 receptor. Recently, a new compound targeting the RAS, namely Aliskerin a drug which inhibits renin has been released on the market.

In the art it is also suggested to use antagonists for Ang II which show a higher binding affinity to AT1 receptor than Ang II. In document WO 2005/044313 A compounds are disclosed which can be used in the treatment of heart diseases, diseases associated with fibrosis and atherosclerosis. The compounds disclosed in WO 2005/044313 A comprise an octapeptide having the general formula $X_1X_2VYIHPX_3$ whereby $X_1$ may be any amino acid residue, $X_2$ arginine or N-alkylated arginine or a mimetic of arginine, and $X_3$ may be an amino acid residue containing a hydrophobic side chain. These compounds have a higher binding affinity to the AT1 receptor than angiotensin II (antagonistic activity).

In GB 2001653 A a compound being derived from angiotensin II and having the general formula XRVYIHPY is disclosed, wherein X represents an α-aminooxy aliphatic acyl group and Y may be leucin, isoleuin, alanin or threonin. Such a compound can be used in the treatment of renal hypertension.

WO 2002/087504 A, WO 2001/043761 A, WO 2001/098325 A and WO 2000/002905 A provide compounds which function as angiotensin II analogues.

Although different drugs to treat hypertension are available on the market, hypertension still remains inadequately handled. Poor overall treatment success lies on the one hand in the asymptomatic nature of hypertension and on the other side in the necessity for long-term treatment with medications that requires at least once daily self-administration.

Recently, active immunotherapy has become of increasing interest as a potential new strategy to treat hypertension and associated disorders.

The practicability of vaccination against components of the RAS to treat hypertension has been shown in different animal models (Michel-J B et al., Am Heart J. 1989; 117: 756). In one of the first approaches it has been shown that vaccination against renin was effective in lowering blood pressure. However, this approach has not been pursued in following years since animals started to suffer from autoimmune nephritis (Michel-J B et al., Circulation. 1990; 81(6): 1899-910). Other approaches aimed at inducing an immune response against components of the RAS that are expressed as transmembrane proteins on the cell surface, such as ACE and AT$_1$R. Several research groups have investigated active immunization against AT$_1$R. Although some studies report that antibodies against the N-terminus of the AT$_1$R can attenuate the development of hypertension in spontaneously hypertensive rats, most approaches had no significant effect on blood pressure. Data on active immunization against ACE is very limited. One report describes the vaccination of rabbits but only 1 out of 50 animals made detectable anti ACE antibodies (Soffer-R L et al., Fed. Proc. 1983; 42(19):2735-9). No reports are available on active immunization against angiotensinogen, however several studies explored the feasibility of vaccination against angiotensin I and angiotensin II.

Vaccination with Ang I conjugated to carrier proteins (e.g. keyhole limpet haemocyanin (KLH)) led to the induction of high antigen-specific humoral immune responses. In experimental settings using different animal models the vaccination-induced antibodies against angiotensin I appeared to be functional, since (i) they were able to bind angiotensin I as revealed by Western blot analysis and (ii) the blood pressure was significantly reduced, indicating that the effects of angiotensin on the RAS were blocked (Downham et al., Br J Clin Pharmacol. 2003; 56:505-12.). By contrast, in human healthy volunteers the blood pressure lowering effect was not seen (Downham et al., 2003). This finding was further confirmed in a study with hypertensive patients who were treated with a 12 amino acid analogue of Ang I covalently linked to KLH and adsorbed to Alum (referred to as PMD3117) (Brown et al., Clin Sci. 2004; 107:167-73). Importantly, this treatment regimen was well tolerated and induced a long lasting, antigen-specific humoral immune response. Additionally, this treatment showed an effect on the renin system as detected by changes in renin and aldosterone levels. However, vaccination with PMD3117 showed no influence on the blood pressure as compared to the placebo control group (Brown et al., 2004). In contrast, a slightly different further development of this Ang I vaccine which was developed by Protherics and replaced Alum by a new adjuvant, namely Co Vaccine HT™ did show an effect. Administration of this new vaccine formulation resulted in a 10-fold increase in anti-angiotensin antibody titers in a preclinical setting and human healthy subjects showed changes in systolic and diastolic blood pressure. However, blood pressure was only slightly reduced and this only during rest periods but not during phases of activity which would be of more importance.

Other approaches to induce antibodies that are able to block the RAS used angiotensin II-derived peptides as antigens. In contrast to a previous study where injection of Ang II-carrier protein conjugates did not result in lowering blood pressure, vaccination with Ang II coupled to virus-like particles (VLP) led to the induction of a high anti-angiotensin specific humoral immune response, that was paralleled with a statistically significant reduction of blood pressure (Ambühl et al., J. Hypertension. 2007; 25:63-72.). In a recent clinical study however, this blood pressure lowering effect could not be monitored upon vaccination using angiotensin II coupled to virus like particles, indicating that the induced humoral immune response induced by this peptide vaccine might not be optimal or sufficient. Therefore, there remains a need in the art to provide new and more effective vaccines targeting angiotensin peptides.

BRIEF SUMMARY OF THE INVENTION

It is an object of the present invention to provide a medication to prevent and treat conditions associated with elevated levels of angiotensin II produced by the RAS on the basis of a vaccine.

It turned out that a vaccine comprising a peptide bound to a pharmaceutically acceptable carrier, said peptide having the amino acid sequence (Formula I) (SEQ ID NO: 1)
$(X_1)_m(X_2)_n(X_3)_o X_4 X_5 HPX_6$, wherein
 $X_1$ is G or D,
 $X_2$ is A, P, M, G, or R,
 $X_3$ is G, A, H, or V,
 $X_4$ is S, A, D, or Y,
 $X_5$ is A, D, H, S, N, or I,
 $X_6$ is A, L or F,
wherein m, n and o are independently 0 or 1 under the premise that when o is 0 m and n are 0 and when n is 0 m is 0, and wherein the peptide is not DRVYIHPF (SEQ ID NO:4) can be suitably used for treating and/or preventing a physical disorder associated with the renin-activated angiotensin system.

Not only peptides having the amino acid sequence according to Formula I can be used for treating and/or preventing a physical disorder associated with the renin-activated angiotensin system, but also peptides having the amino acid sequences according to Formula II and III. Therefore, another aspect of the present invention relates to a vaccine comprising a peptide bound to a pharmaceutically acceptable carrier, said peptide having the amino acid sequence (Formula II) (SEQ ID NO: 2)
$(X_1)_m(X_2)_n(X_3)_o X_4 X_5 X_6 PX_7$, for treating and/or preventing a physical disorder associated with the renin-activated angiotensin system, wherein
 $X_1$ is G, A or D,
 $X_2$ is A, P, M, G, or R,
 $X_3$ is G, A, H, or V,
 $X_4$ is S, A, D, or Y,
 $X_5$ is A, D, H, S, N, or I,
 $X_6$ is Y or H,
 $X_7$ is A, V, L, I or F,
wherein m, n and o are independently 0 or 1 under the premise that when o is 0 m and n are 0 and when n is 0 m is 0, and wherein the peptide is not DRVYIHPF (SEQ ID NO:4).

According to a particularly preferred embodiment of the present invention the vaccine comprises a peptide having the amino acid sequence (Formula III) (SEQ ID NO: 3)
$X_1 X_2 X_3 X_4 X_5 X_6 PX_7$ which can be used for treating and/or preventing physical disorders associated with the renin-activated angiotensin system, preferably hypertension and hypertension-associated diseases, wherein
 $X_1$ is G, A or D,
 $X_2$ is A, P, M, G, or R,
 $X_3$ is G, A, H, or V,
 $X_4$ is S, A, D, or Y,
 $X_5$ is A, D, H, S, N, or I,
 $X_6$ is Y or H,
 $X_7$ is A, V, L, I or F.
wherein the peptide is not DRVYIHPF (SEQ ID NO:4).

BRIEF DESCRIPTION OF THE DRAWINGS

The present invention is further illustrated in the following figures and examples, however, without being restricted thereto.

Figure 1:
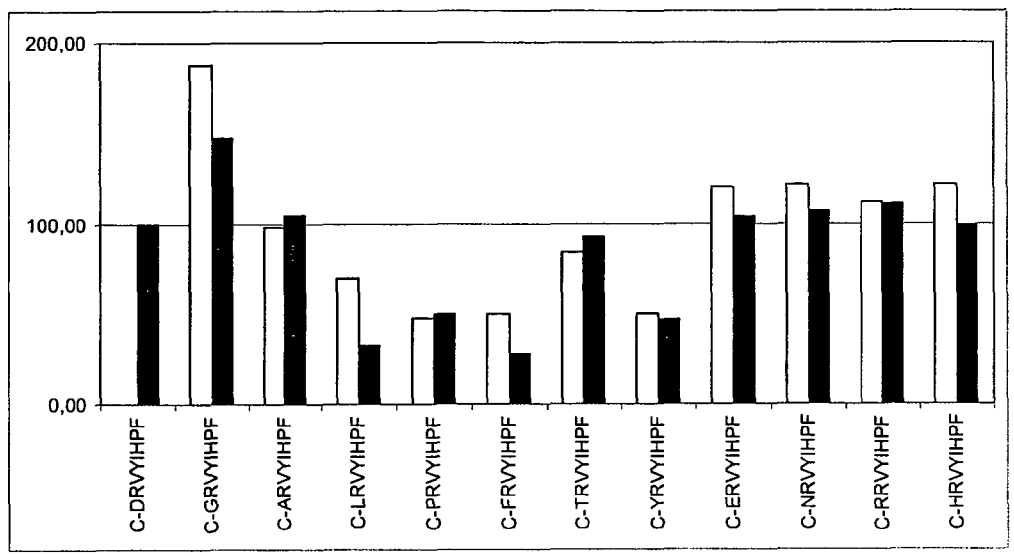
FIG. 1 shows the immunogenicity of peptide variants for position 1 of Ang II peptide CDRVYIHPF (SEQ ID NO:235).

In each Figure, on the X-axis sera derived from animals immunized with indicated peptides are listed. On the Y-axis relative titers of induced sera are shown. Titers derived from Ang II treated animals were set as 100%. Titers were calculated as the sera dilution giving half-maximal binding (i.e. $OD_{max}/2$). White bars indicate titers against the peptides that were used for vaccination while black bars represent titers against the Ang II peptide.

DETAILED DESCRIPTION OF THE INVENTION

The vaccine of the present invention is able to induce specifically the formation of antibodies directed to angiotensin I or angiotensin II when coupled to a carrier protein (or to a peptide containing a T cell epitope) and administered to a mammal. The peptides as outlined in Formulas I to III, may induce antibodies that recognize Ang II with higher specificity than Ang I. Vaccines comprising a peptide having the sequence as outlined in Formulas I to III and having H, and L on their C-terminus $X_1X_2X_3X_4X_5X_6PX_7HL$ (both amino acids derived from Ang I), for instance, induce antibodies that may recognize Ang I with higher specificity than Ang II. This allows the specific targeting of either only one species of angiotensin peptides or a combination thereof. Due to the binding of these antibodies to angiotensinogen-derived peptides in said mammals the level of angiotensin peptides can be influenced significantly, and thus these immunogens can be used in an immunotherapeutic approach to combat conditions associated with elevated levels of angiotensin II produced by the RAS or by other proteases (e.g. chymase). Without intending to be limited to any particular theory of mode of molecular action, the peptide variants of the present invention will act as immunogens that can induce antibodies which bind to more than one angiotensin peptide species, thus neutralizing all relevant species of angiotensin peptides at the same time. Alternatively, the induced antibodies can specifically bind to the C-terminus of angiotensin II. Under these conditions the induced antibodies will additionally block the binding of angiotensin II to its receptor, the $AT_1R$.

The amino acid residues identified in Formulas I to III can be exchanged by the respective amino acid residues indicated above. The amino acid sequence obtained by said variation may comprise one, two, three, four, five, six or seven amino acid residues which are not identical to the original Angiotensin II sequence (DRVYIHPF) (SEQ ID NO:4). Most preferably Formulas I to III may vary from the Angiotensin II sequence by at least one, more preferably by at least two, amino acid residues and by a maximum of seven, preferably by a maximum of six, more preferably by a maximum of five, more preferably by a maximum of four, even more preferably by a maximum of three amino acid residues.

The peptides of the above identified Formulas may also comprise five, six, seven or eight amino acid residues (starting from $X_1$ or $X_2$ or $X_3$ to the terminal amino acid residue).

The peptide according to the present invention may be a peptide with 5, 6, 7 or 8 to 20, preferably with 5, 6, 7 or 8 to 15, in particular with 5, 6, 7, 8 or 9, amino acid residues. The peptide of the present invention may also be part of a polypeptide or protein having up to 300, preferably up to 200, more preferably up to 150, even more preferably up to 100, amino acid residues.

The peptides of the present invention are not identical to the naturally occurring angiotensin II (DRVYIHPF) (SEQ ID NO:4). The vaccine of the present invention will elicit an immunological response in a host that is reactive to angiotensin peptides.

The peptides of the present invention can be synthetically produced by chemical synthesis methods which are well known in the art, either as an isolated peptide or as a part of another peptide or polypeptide. Alternatively, the peptide can be produced in a microorganism which produces the peptide which is then isolated and if desired, further purified. The peptide variant can be produced in microorganisms such as bacteria, yeast or fungi, in eukaryote cells such as a mammalian or an insect cell, or in a recombinant virus vector such as adenovirus, poxvirus, herpesvirus, Simliki forest virus, baculovirus, bacteriophage, sindbis virus or sendai virus. Suitable bacteria for producing the compound/peptide include *E. coli, B. subtilis* or any other bacterium that is capable of expressing peptides. Suitable yeast types for expressing said compound/peptide include Saccharomyces cerevisiae, *Schizosaccharomyces pombe, Candida, Pichia pastoris* or any other yeast capable of expressing peptides. Corresponding methods are well known in the art. Also methods for isolating and purifying recombinantly produced peptides are well known in the art and include e.g. as gel filtration, affinity chromatography, ion exchange chromatography etc.

To facilitate isolation of the peptide, a fusion polypeptide may be made wherein the peptide is translationally fused (covalently linked) to a heterologous polypeptide which enables isolation by affinity chromatography. Typical heterologous polypeptides are His-Tag (e.g. His6; 6 histidine residues), GST-Tag (Glutathione-S-transferase) etc. The fusion polypeptide facilitates not only the purification of the peptide but may also prevent the degradation of said peptide during purification. If it is desired to remove the heterologous polypeptide after purification, the fusion polypeptide may comprise a cleavage site at the junction between the peptide and the heterologous polypeptide. The cleavage site consists of an amino acid sequence that is cleaved with an enzyme specific for the amino acid sequence at the site (e.g. proteases).

"Peptide bound to a pharmaceutically acceptable carrier" and "peptide bound to a carrier", as used herein refers to a peptide which is fused to, or conjugated to a carrier. If the peptide of the present invention is fused or conjugated (e.g. via carboxyl, amino, sulfhydryl, hydroxyl, imidazolyl, guanidyl or indolyl groups) to a protein carrier, a linker may be provided between the peptide and the protein carrier.

According to a particularly preferred embodiment of the present invention the substituents of Formula I may be as follows:

$X_1$ is G or D,
$X_2$ is G, R, A, P or M
$X_3$ is A, V or G
$X_4$ is Y, A or S
$X_5$ is N, I, D, S or A and/or
$X_6$ is F.

According to a preferred embodiment of the present invention the peptide derived from Formula I is selected from the group consisting of GRVYIHPF (SEQ ID NO:6), DPVYIHPF (SEQ ID NO:7), DMVYIHPF (SEQ ID NO:8), DGVYIHPF (SEQ ID NO:9), DAVYIHPF (SEQ ID NO:10), DRGYIHPF (SEQ ID NO:11), DRAYIHPF (SEQ ID NO:12), DRHYIHPF (SEQ ID NO:13), DRVAIHPF (SEQ ID NO:14), DRVSIHPF (SEQ ID NO:15), DRVDIHPF (SEQ ID NO:16), DRVYAHPF (SEQ ID NO:17), DRVYNHPF (SEQ ID NO:18), DRVYDHPF (SEQ ID NO:19), DRVYHHPF (SEQ ID NO:20), DRVYSHPF (SEQ ID NO:21), DRVYIHPA (SEQ ID NO:23), DRVYIHPL (SEQ ID NO:25), DAAYIHPF (SEQ ID NO:27), DRAAIHPF (SEQ ID NO:28), DRVAAHPF (SEQ ID NO:29), DRAYAHPF (SEQ ID NO:30), DRAAAHPF (SEQ ID NO:31), DAAAIHPF (SEQ ID NO:34), DAGYIHPF (SEQ ID NO:37), DAHYIHPF (SEQ ID NO:38), DPGYIHPF (SEQ ID NO:39), DPAYIHPF (SEQ ID NO:40), DMGYIHPF (SEQ ID NO:41), DMAYIHPF (SEQ ID NO:42), DMHYIHPF (SEQ ID NO:43), DGGYIHPF (SEQ ID NO:44), DGAYIHPF (SEQ ID NO:45), DGHYIHPF (SEQ ID NO:46), DPVAIHPF (SEQ ID NO:47), DMVAIHPF (SEQ ID NO:49), DMVSIHPF (SEQ ID NO:50), DRGAIHPF (SEQ ID NO:51), DRHAIHPF (SEQ ID NO:52), DRGYAHPF (SEQ ID NO:53), DRGYDHPF (SEQ ID NO:54), DRGYHPF (SEQ ID NO:55), DRGYSHPF (SEQ ID NO:56), DRGYNHPF (SEQ ID NO:57), DRAYDHPF (SEQ ID NO:58), DRAYHHPF (SEQ ID NO:59), DRAYSHPF (SEQ ID NO:60), DRAYNHPF (SEQ ID NO:61), DRHYAHPF (SEQ ID NO:62), DRHYSHPF (SEQ ID NO:63), DRHYNHPF (SEQ ID NO:64), DRHYDHPF (SEQ ID NO:65), DRHYHHPF (SEQ ID NO:66), DRGADHPF (SEQ ID NO:68), DRVAHHPF (SEQ ID NO:70), DRHADHPF (SEQ ID NO:71), GRGAIHPF (SEQ ID NO:72), DPGAIHPF (SEQ ID NO:75), DPGSIHPF (SEQ ID NO:77), DMGAIHPF (SEQ ID NO:78), DMGSIHPF (SEQ ID NO:79), GPGYIHPF (SEQ ID NO:80), GPGSIHPF (SEQ ID NO:82), GMGSIHPF (SEQ ID NO:83), DRGSIHPF (SEQ ID NO:84), DPHAIHPF (SEQ ID NO:85), DMHAIHPF (SEQ ID NO:86), GPHAIHPF (SEQ ID NO:87), GMHSIHPF (SEQ ID NO:90), PVYIHPF (SEQ ID NO:91), MVYIHPF (SEQ ID NO:92), GVYIHPF (SEQ ID NO:93), AVYIHPF (SEQ ID NO:94), RGYIHPF (SEQ ID NO:95), RAYIHPF (SEQ ID NO:96), RHYIHPF (SEQ ID NO:97), RVAIHPF (SEQ ID NO:98), RVSIHPF (SEQ ID NO:99), RVDIHPF (SEQ ID NO:100), RVYAHPF (SEQ ID NO:101), RVYNHPF (SEQ ID NO:102), RVYDHPF (SEQ ID NO:103), RVYHHPF (SEQ ID NO:104), RVYSHPF (SEQ ID NO:105), RVYIHPA (SEQ ID NO:107), RVYIHPL (SEQ ID NO:109), AAYIHPF (SEQ ID NO:111), RAAIHPF (SEQ ID NO:112), RVAAHPF (SEQ ID NO:113), RAYAHPF (SEQ ID NO:114), RAAAHPF (SEQ ID NO:115), AAAIHPF (SEQ ID NO:118), AGYIHPF (SEQ ID NO:121), AHYIHPF (SEQ ID NO: 122), PGYIHPF (SEQ ID NO:123), PAYIHPF (SEQ ID NO:124), MGYIHPF (SEQ ID NO:125), MAYIHPF (SEQ ID NO:126), MHYIHPF (SEQ ID NO:127), GGYIHPF (SEQ ID NO:128), GAYIHPF (SEQ ID NO:129), GHYIHPF (SEQ ID NO:130), PVAIHPF (SEQ ID NO:131), PVSIHPF (SEQ ID NO: 132), MVAIHPF (SEQ ID NO:133), MVSIHPF (SEQ ID NO:134), RGAIHPF (SEQ ID NO:135), RHAIHPF (SEQ ID NO: 136), RGYAHPF (SEQ ID NO:137), RGYDHPF (SEQ ID NO:138), RGYHHPF (SEQ ID NO:139), RGYSHPF (SEQ ID NO:140), RGYNHPF (SEQ ID NO:141), RAYDHPF (SEQ ID NO:142), RAYHHPF (SEQ ID NO:143), RAYSHPF (SEQ ID NO:144), RAYNHPF (SEQ ID NO:145), RHYAHPF (SEQ ID NO:146), RHYSHPF (SEQ ID NO:147), RHYNHPF (SEQ ID NO:148), RHYDHPF (SEQ ID NO:149), RHYHHPF (SEQ ID NO:150), RGADHPF (SEQ ID NO: 152), RGAHHPF (SEQ ID NO:153), RHADHPF (SEQ ID NO:155), RHSIHPF (SEQ ID NO:157), PGAIHPF (SEQ ID NO:159), RHAIHPF (SEQ ID NO: 136), PGSIHPF (SEQ ID NO:161), MGAIHPF (SEQ ID NO:162), MGSIHPF (SEQ ID NO:163), RGSIHPF (SEQ ID NO:166), PHAIHPF (SEQ ID NO:167), MHAIHPF (SEQ ID NO:168), PHSIHPF (SEQ ID NO:169), MHSIHPF (SEQ ID NO:170), GYIHPF (SEQ ID NO:171), AYIHPF (SEQ ID NO:172), HYIHPF (SEQ ID NO:173), VYAHPF (SEQ ID NO:176), VYNHPF (SEQ ID NO:177), VYDHPF (SEQ ID NO:178), VYHHPF (SEQ ID NO:179), VYSHPF (SEQ ID NO:180), VYIHPA (SEQ ID NO:182), VYIHPL (SEQ ID NO:184), AAIHPF (SEQ ID NO:186), AYAHPF (SEQ ID NO:188), HYIHPF (SEQ ID NO:173), GAIHPF (SEQ ID NO:192), HAIHPF (SEQ ID NO:193), GYAHPF (SEQ ID NO:194), GYDHPF (SEQ ID NO:195), GYHHPF (SEQ ID NO:196), GYSHPF (SEQ ID NO:197), GYNHPF (SEQ ID NO:198), AYDHPF (SEQ ID NO:199), AYHHPF (SEQ ID NO:200), AYSHPF (SEQ ID NO:201), AYNHPF (SEQ ID NO:202), HYAHPF (SEQ ID NO:203), HYSHPF (SEQ ID NO:204), HYNHPF (SEQ ID NO:205), HYDHPF (SEQ ID NO:206), HYHHPF (SEQ ID NO:207), GAIHPF (SEQ ID NO:192), HSIHPF (SEQ ID NO:214), GSIHPF (SEQ ID NO:216), HAIHPF (SEQ ID NO:193), AIHPF (SEQ ID NO:218), SIHPF (SEQ ID NO:219), DIHPF (SEQ ID NO:220), YAHPF (SEQ ID NO:221), YNHPF (SEQ ID NO:222), YDHPF (SEQ ID NO:223), YHHPF (SEQ ID NO:224) and YSHPF (SEQ ID NO:225).

Particularly preferred peptides are DPVYIHPF (SEQ ID NO:7), DMVYIHPF (SEQ ID NO:8), DGVYIHPF (SEQ ID NO:9), DAVYIHPF (SEQ ID NO:10), DRGYIHPF (SEQ ID NO:11), DRAYIHPF (SEQ ID NO:12), DRHYIHPF (SEQ ID NO:13), DRVAIHPF (SEQ ID NO:14), DRVYAHPF (SEQ ID NO: 17), DRVYNHPF (SEQ ID NO:18), DRVYDHPF (SEQ ID NO:19), DRVYSHPF (SEQ ID NO:21), DRVYIHPL (SEQ ID NO:25), DAAYIHPF (SEQ ID NO:27), DRAAIHPF (SEQ ID NO:28), DRVAAHPF (SEQ ID NO:29), DRAYAHPF (SEQ ID NO:30), DAGYIHPF (SEQ ID NO:37), DAHYIHPF (SEQ ID NO:38), DPGYIHPF (SEQ ID NO:39), DPAYIHPF (SEQ ID NO:40), DMGYIHPF (SEQ ID NO:41), DMAYIHPF (SEQ ID NO:42), DMHYIHPF (SEQ ID NO:43), DGGYIHPF (SEQ ID NO:44), DGAYIHPF (SEQ ID NO:45), DGHYIHPF (SEQ ID NO:46), DMVSIHPF (SEQ ID NO:50), DRGAIHPF (SEQ ID NO:51), DRGYAHPF (SEQ ID NO:53), DRGYDHPF (SEQ ID NO:54), DRGYSHPF (SEQ ID NO:56), DRGYNHPF (SEQ ID NO:57), DRAYDHPF (SEQ ID NO:58), DRAYSHPF (SEQ ID NO:60), DRAYNHPF (SEQ ID NO:61), DRHYAHPF (SEQ ID NO:62), DRHYSHPF (SEQ ID NO:63), DRHYNHPF (SEQ ID NO:64), DRHYDHPF (SEQ ID NO:65), GPGYIHPF (SEQ ID NO:80), GPGSIHPF (SEQ ID NO:82), DRGSIHPF (SEQ ID NO:84), PVYIHPF (SEQ ID NO:91), GVYIHPF (SEQ ID NO:93), AVYIHPF (SEQ ID NO: 94), RGYIHPF (SEQ ID NO: 95), RAYIHPF (SEQ ID NO: 96), RHYIHPF (SEQ ID NO:97), RVAIHPF (SEQ ID NO:98), RVSIHPF (SEQ ID NO:99), RVDIHPF (SEQ ID NO:100), RVYAHPF (SEQ ID NO:101), RVYNHPF (SEQ ID NO:102), RVYDHPF (SEQ ID NO:103), RVYSHPF (SEQ ID NO:105), RVYIHPL (SEQ ID NO:109), AAYIHPF (SEQ ID NO:111), RAAIHPF (SEQ ID NO:112), RVAAHPF (SEQ ID NO:113), RAYAHPF (SEQ ID NO:114), AGYIHPF (SEQ ID NO:121), AHYIHPF (SEQ ID NO:122), PGYIHPF (SEQ ID NO:123), PAYIHPF (SEQ ID NO:124), GGYIHPF (SEQ ID NO:128), GAYIHPF (SEQ ID NO:129), GHYIHPF (SEQ ID NO:130), PVSIHPF (SEQ ID NO:132), MVSIHPF (SEQ ID NO:134), RGAIHPF (SEQ ID NO:135), RGYAHPF (SEQ ID NO:137), RGYDHPF (SEQ ID NO:138), RGYSHPF (SEQ ID NO:140), RGYNHPF (SEQ ID NO:141), RAYDHPF (SEQ ID NO:142), RAYSHPF (SEQ ID NO:144), RAYNHPF (SEQ ID NO:145), RHYAHPF (SEQ ID NO:146), RHYSHPF (SEQ ID NO:147), RHYNHPF (SEQ ID NO:148), RHYDHPF (SEQ ID NO:149), RHSIHPF (SEQ ID NO:157), PGAIHPF (SEQ ID NO:159), RHAIHPF (SEQ ID NO:136), PGSIHPF (SEQ ID NO:161), MGAIHPF (SEQ ID NO:162), MGSIHPF (SEQ ID NO:163), MGYIHPF (SEQ ID NO:125), RGSIHPF (SEQ ID NO:166), PHAIHPF (SEQ ID NO:167), MHAIHPF (SEQ ID NO:168), PHSIHPF (SEQ ID NO:169), MHSIHPF (SEQ ID NO:170), GYIHPF (SEQ ID NO:171), AYIHPF (SEQ ID NO:172), VYAHPF (SEQ ID NO:176), VYNHPF (SEQ ID NO:177), VYDHPF (SEQ ID NO:178), VYSHPF (SEQ ID NO:180), AAIHPF (SEQ ID NO:186), AYAHPF (SEQ ID NO:188), HYIHPF (SEQ ID NO:173), GAIHPF (SEQ ID NO:192), GYAHPF (SEQ ID NO:194), GYDHPF (SEQ ID NO:195), GYSHPF (SEQ ID NO:197), GYNHPF (SEQ ID NO:198), AYDHPF (SEQ ID NO:199), AYSHPF (SEQ ID NO:201), AYNHPF (SEQ ID NO:202), GAIHPF (SEQ ID NO:192), GSIHPF (SEQ ID NO:216).

Even more preferred peptides are DPVYIHPF (SEQ ID NO:7), DMVYIHPF (SEQ ID NO:8), DGVYIHPF (SEQ ID NO:9), DAVYIHPF (SEQ ID NO:10), DRGYIHPF (SEQ ID NO:11), DRAYIHPF (SEQ ID NO:12), DRHYIHPF (SEQ ID NO:13), DRVYIHPL (SEQ ID NO:25), DAAYIHPF (SEQ ID NO:27), DRAAIHPF (SEQ ID NO:28), DRVAAHPF (SEQ ID NO:29), DRAYAHPF (SEQ ID NO:30), DAGYIHPF (SEQ ID NO:37), DAHYIHPF (SEQ ID NO:38), DPGYIHPF (SEQ ID NO:39), DPAYIHPF (SEQ ID NO:40), DMGYIHPF (SEQ ID NO:41), DMAYIHPF (SEQ ID NO:42), DMHYIHPF (SEQ ID NO:43), DGGYIHPF (SEQ ID NO:44), DGAYIHPF (SEQ ID NO:45), DGHYIHPF (SEQ ID NO:46), DMVSIHPF (SEQ ID NO:50), DRGAIHPF (SEQ ID NO:51), DRGYAHPF (SEQ ID NO:53), DRGYDHPF (SEQ ID NO:54), DRGYSHPF (SEQ ID NO:56), DRGYNHPF (SEQ ID NO:57), DRAYDHPF (SEQ ID NO:58), DRAYSHPF (SEQ ID NO:60), DRAYNHPF (SEQ ID NO:61), GPGYIHPF (SEQ ID NO:80), PVYIHPF (SEQ ID NO: 91), GVYIHPF (SEQ ID NO:93), RGYIHPF (SEQ ID NO:95), RAYIHPF (SEQ ID NO:96), RVSIHPF (SEQ ID NO:99), RVYIHPL (SEQ ID NO:109), AAYIHPF (SEQ ID NO:111), RAAIHPF (SEQ ID NO:112), RAYAHPF (SEQ ID NO:114), AGYIHPF (SEQ ID NO:121), PGYIHPF (SEQ ID NO:123), PAYIHPF (SEQ ID NO:124), GAYIHPF (SEQ ID NO:129), PVSIHPF (SEQ ID NO:132), MVSIHPF (SEQ ID NO:134), RGAIHPF (SEQ ID NO:135), RGYAHPF (SEQ ID NO:137), RGYSHPF (SEQ ID NO:140), GYIHPF (SEQ ID NO:171), whereby the most preferred peptides are DPVYIHPF (SEQ ID NO:7), DMVYIHPF (SEQ ID NO:8), DAAYIHPF (SEQ ID NO:27), DRAAIHPF (SEQ ID NO:28), DRAYAHPF (SEQ ID NO:30), DAGYIHPF (SEQ ID NO:37), DPGYIHPF (SEQ ID NO:39), DGAYIHPF (SEQ ID NO:45), DMVSIHPF (SEQ ID NO:50), DRGAIHPF (SEQ ID NO:51), DRGYDHPF (SEQ ID NO:54), DRGYSHPF (SEQ ID NO:56), PVYIHPF (SEQ ID NO:91), GVYIHPF (SEQ ID NO:93), AAYIHPF (SEQ ID NO:111), RAAIHPF (SEQ ID NO:112), RAYAHPF (SEQ ID NO: 114), PGYIHPF (SEQ ID NO:123), PVSIHPF (SEQ ID NO:132), MVSIHPF (SEQ ID NO:134), RGAIHPF (SEQ ID NO:135).

According to a preferred embodiment of the present invention $X_1$ of Formula II and III is G, A or D, $X_2$ of Formula II and III is G, A, P, M, or R $X_3$ of Formula II and III is G, A, H, or V $X_4$ of Formula II and III is S, A, D, or Y $X_5$ of Formula II and III is A, D, H, S, N or I $X_6$ of Formula II and III is Y or H $X_7$ of Formula II and III is A, V, L, I or F.

The amino acid residues mentioned above are particularly preferred substitutes.

The peptides of the present invention may comprise a truncation at their N-terminus, so that these peptides miss the first, second and/or third amino acid residue.

The peptide is preferably selected from the group consisting of GRVYIHPF (SEQ ID NO:6), DPVYIHPF (SEQ ID NO:7), DMVYIHPF (SEQ ID NO:8), DGVYIHPF (SEQ ID NO:9), DAVYIHPF (SEQ ID NO:10), DRGYIHPF (SEQ ID NO:11), DRAYIHPF (SEQ ID NO:12), DRHYIHPF (SEQ ID NO:13), DRVAIHPF (SEQ ID NO:14), DRVSIHPF (SEQ ID NO:15), DRVDIHPF (SEQ ID NO:16), DRVYAHPF (SEQ ID NO: 17), DRVYNHPF (SEQ ID NO:18), DRVYDHPF (SEQ ID NO:19), DRVYHHPF (SEQ ID NO:20), DRVYSHPF (SEQ ID NO:21), DRVYIYPF (SEQ ID NO:22), DRVYIHPA (SEQ ID NO:23), DRVYIHPV (SEQ ID NO:24), DRVYIHPL (SEQ ID NO:25), DRVYIHPI (SEQ ID NO:26), DAAYIHPF (SEQ ID NO:27), DRAAIHPF (SEQ ID NO:28), DRVAAHPF (SEQ ID NO:29), DRAYAHPF (SEQ ID NO:30), DRAAAHPF (SEQ ID NO:31), ARAAIHPF (SEQ ID NO:32), ARVAAHPF (SEQ ID NO:33), DAAAIHPF (SEQ ID NO:34), DAAAAHPF (SEQ ID NO:35), DAVAAHPF (SEQ ID NO:36), DAGYIHPF (SEQ ID NO:37), DAHYIHPF (SEQ ID NO:38), DPGYIHPF (SEQ ID NO:39), DPAYIHPF (SEQ ID NO:40), DMGYIHPF (SEQ ID NO:41), DMAYIHPF (SEQ ID NO:42), DMHYIHPF (SEQ ID NO:43), DGGYIHPF (SEQ ID NO:44), DGAYIHPF (SEQ ID NO:45), DGHYIHPF (SEQ ID NO:46), DPVAIHPF (SEQ ID NO:47), DPVSIHPF (SEQ ID NO:48), DMVAIHPF (SEQ ID NO:49), DMVSIHPF (SEQ ID NO:50), DRGAIHPF (SEQ ID NO:51), DRHAIHPF (SEQ ID NO:52), DRGYAHPF (SEQ ID NO:53), DRGYDHPF (SEQ ID NO:54), DRGYHHPF (SEQ ID NO:55), DRGYSHPF (SEQ ID NO:56), DRGYNHPF (SEQ ID NO:57), DRAYDHPF (SEQ ID NO:58), DRAYHHPF (SEQ ID NO:59), DRAYSHPF (SEQ ID NO:60), DRAYNHPF (SEQ ID NO:61), DRHYAHPF (SEQ ID NO:62), DRHYSHPF (SEQ ID NO:63), DRHYNHPF (SEQ ID NO:64), DRHYDHPF (SEQ ID NO:65), DRHYHHPF (SEQ ID NO:66), DRHYIYPF (SEQ ID NO:67), DRGADHPF (SEQ ID NO:68), DRGAHHPF (SEQ ID NO:69), DRVAHHPF (SEQ ID NO:70), DRHADHPF (SEQ ID NO:71), GRGAIHPF (SEQ ID NO:72), GRHSIHPF (SEQ ID NO:73), GRHADYPF (SEQ ID NO:74), DPGAIHPF (SEQ ID NO:75), GRHAIHPF (SEQ ID NO:76), DPGSIHPF (SEQ ID NO:77), DMGAIHPF (SEQ ID NO:78), DMGSIHPF (SEQ ID NO:79), GPGYIHPF (SEQ ID NO:80), GMGYIHPF (SEQ ID NO:81), GPGSIHPF (SEQ ID NO:82), GMGSIHPF (SEQ ID NO:83), DRGSIHPF (SEQ ID NO:84), DPHAIHPF (SEQ ID NO:85), DMHAIHPF (SEQ ID NO:86), GPHAIHPF (SEQ ID NO:87), GMHAIHPF (SEQ ID NO:88), GPHSIHPF (SEQ ID NO:89), and GMHSIHPF (SEQ ID NO:90).

Truncated versions missing the first N-terminal amino acid residue are preferably selected from the group consisting of PVYIHPF (SEQ ID NO:91), MVYIHPF (SEQ ID NO:92), GVYIHPF (SEQ ID NO:93), AVYIHPF (SEQ ID NO:94), RGYIHPF (SEQ ID NO:95), RAYIHPF (SEQ ID NO:96), RHYIHPF (SEQ ID NO:97), RVAIHPF (SEQ ID NO:98), RVSIHPF (SEQ ID NO:99), RVDIHPF (SEQ ID NO:100), RVYAHPF (SEQ ID NO:101), RVYNHPF (SEQ ID NO:102), RVYDHPF (SEQ ID NO:103), RVYHHPF (SEQ ID NO:104), RVYSHPF (SEQ ID NO:105), RVYIYPF (SEQ ID NO:106), RVYIHPA (SEQ ID NO:107), RVYIHPV (SEQ ID NO:108), RVYIHPL (SEQ ID NO:109), RVYIHPI (SEQ ID NO:110), AAYIHPF (SEQ ID NO:111), RAAIHPF (SEQ ID NO:112), RVAAHPF (SEQ ID NO:113), RAYAHPF (SEQ ID NO:114), RAAAHPF (SEQ ID NO:115), RAAIHPF (SEQ ID NO:112), RVAAHPF (SEQ ID NO:113), AAAIHPF (SEQ ID NO:118), AAAAHPF (SEQ ID NO:119), AVAAHPF (SEQ ID NO:120), AGYIHPF (SEQ ID NO:121), AHYIHPF (SEQ ID NO:122), PGYIHPF (SEQ ID NO:123), PAYIHPF (SEQ ID NO:124), MGYIHPF (SEQ ID NO:125), MAYIHPF (SEQ ID NO:126), MHYIHPF (SEQ ID NO:127), GGYIHPF (SEQ ID NO:128), GAYIHPF (SEQ ID NO:129), GHYIHPF (SEQ ID NO:130), PVAIHPF (SEQ ID NO:131), PVSIHPF (SEQ ID NO:132), MVAIHPF (SEQ ID NO:133), MVSIHPF (SEQ ID NO:134), RGAIHPF (SEQ ID NO:135), RHAIHPF (SEQ ID NO:136), RGYAHPF (SEQ ID NO:137), RGYDHPF (SEQ ID NO:138), RGYHHPF (SEQ ID NO:139), RGYSHPF (SEQ ID NO:140), RGYNHPF (SEQ ID NO:141), RAYDHPF (SEQ ID NO:142), RAYHHPF (SEQ ID NO:143), RAYSHPF (SEQ ID NO:144), RAYNHPF (SEQ ID NO:145), RHYAHPF (SEQ ID NO:146), RHYSHPF (SEQ ID NO:147), RHYNHPF (SEQ ID NO:148), RHYDHPF (SEQ ID NO:149), RHYHHPF (SEQ ID NO:150), RHYIYPF (SEQ ID NO:151), RGADHPF (SEQ ID NO:152), RGAHHPF (SEQ ID NO:153), RVAHHPF (SEQ ID NO:154), RHADHPF (SEQ ID NO:155), RHSIHPF (SEQ ID NO:157), RHADYPF (SEQ ID NO:158), PGAIHPF (SEQ ID NO:159), RHAIHPF (SEQ ID NO:136), PGSIHPF (SEQ ID NO:161), MGAIHPF (SEQ ID NO:162), MGSIHPF (SEQ ID NO:163), RGSIHPF (SEQ ID NO:166), PHAIHPF (SEQ ID NO:167), MHAIHPF (SEQ ID NO:168), PHSIHPF (SEQ ID NO:169), and MHSIHPF (SEQ ID NO:170).

Truncated versions missing the first two N-terminal amino acid residues are preferably selected from the group consisting of GYIHPF (SEQ ID NO:171), AYIHPF (SEQ ID NO:172), HYIHPF (SEQ ID NO:173), VAIHPF (SEQ ID NO:174), VSIHPF (SEQ ID NO:191), VDIHPF (SEQ ID NO:175), VYAHPF (SEQ ID NO:176), VYNHPF (SEQ ID NO:177), VYDHPF (SEQ ID NO:178), VYHHPF (SEQ ID NO:179), VYSHPF (SEQ ID NO:180), VYIYPF (SEQ ID NO:181), VYIHPA (SEQ ID NO:182), VYIHPV (SEQ ID NO:183), VYIHPL (SEQ ID NO:184), VYIHPI (SEQ ID NO:185), AAIHPF (SEQ ID NO:186), VAAHPF (SEQ ID NO:187), AYAHPF (SEQ ID NO:188), AAAHPF (SEQ ID NO:189), HYIHPF (SEQ ID NO:173), GAIHPF (SEQ ID NO:192), HAIHPF (SEQ ID NO:193), GYAHPF (SEQ ID NO:194), GYDHPF (SEQ ID NO:195), GYHHPF (SEQ ID NO:196), GYSHPF (SEQ ID NO:197), GYNHPF (SEQ ID NO:198), AYDHPF (SEQ ID NO:199), AYHHPF (SEQ ID NO:200), AYSHPF (SEQ ID NO:201), AYNHPF (SEQ ID NO:202), HYAHPF (SEQ ID NO:203), HYSHPF (SEQ ID NO:204), HYNHPF (SEQ ID NO:205), HYDHPF (SEQ ID NO:206), HYHHPF (SEQ ID NO:207), HYIYPF (SEQ ID NO:208), GADHPF (SEQ ID NO:209), GAHHPF (SEQ ID NO:210), VAHHPF (SEQ ID NO:211), HADHPF (SEQ ID NO:212), GAIHPF (SEQ ID NO:192), HSIHPF (SEQ ID NO:214), HADYPF (SEQ ID NO:215), GSIHPF (SEQ ID NO:216), and HAIHPF (SEQ ID NO:193).

Truncated versions missing the first three N-terminal amino acid residues are preferably selected from the group consisting of AIHPF (SEQ ID NO:218), SIHPF (SEQ ID NO:219), DIHPF (SEQ ID NO:220), YAHPF (SEQ ID NO:221), YNHPF (SEQ ID NO:222), YDHPF (SEQ ID NO:223), YHHPF (SEQ ID NO:224), YSHPF (SEQ ID NO:225), YIYPF (SEQ ID NO:226), YIHPA (SEQ ID NO:227), YIHPV (SEQ ID NO:228), YIHPL (SEQ ID NO:229), YIHPI (SEQ ID NO:230), AAHPF (SEQ ID NO:231), ADHPF (SEQ ID NO:232), AHHPF (SEQ ID NO:233), and ADYPF (SEQ ID NO:234).

According to a preferred embodiment of the present invention at least one cysteine residue is bound to the N-terminus of the amino acid sequences according to Formula I, II and/or III and all specific peptides mentioned above.

The peptide of the present invention may further comprise at least one cysteine residue at its N-terminus. This cysteine residue may serve as a reactive group in order to bind the peptide to another molecule or a carrier. For instance, this group may be used to bind the peptide to a carrier protein. The cysteine residue may alternatively be bound to the C-terminus of the peptide of the present invention.

The peptide of the present invention is bound to a carrier, preferably protein carrier.

In order to enhance the production of angiotensin peptide specific antibodies in a mammal the compound of the present invention is bound to a carrier.

According to a preferred embodiment of the present invention the carrier is selected from the group consisting of keyhole limpet haemocyanin (KLH), tetanus toxoid (TT) or diphtheria toxin (DT) or any other protein or peptide containing T cell epitopes.

According to a preferred embodiment of the present invention the peptide is coupled to a pharmaceutically acceptable carrier, preferably KLH (Keyhole Limpet Haemocyanin), tetanus toxoid, albumin-binding protein, bovine serum albumin, a dendrimer (MAP; Biol. Chem. 358: 581), peptide linkers (or flanking regions) as well as the adjuvant substances described in Singh et al., Nat. Biotech. 17 (1999), 1075-1081 (in particular those in Table 1 of that document), and O'Hagan et al., Nature Reviews, Drug Discovery 2 (9) (2003), 727-735 (in particular the endogenous immuno-potentiating compounds and delivery systems described therein), or mixtures thereof. The conjugation chemistry (e.g. via heterobifunctional compounds such as GMBS and of course also others as described in "Bioconjugate Techniques", Greg T. Hermanson) in this context can be selected from reactions known to the skilled man in the art. Moreover, the vaccine composition may be formulated with an adjuvant, preferably a low soluble aluminium composition, in particular aluminium hydroxyide. Of course, also adjuvants like MF59 aluminium phosphate, calcium phosphate, cytokines (e.g., IL-2, IL-12, GM-CSF), saponins (e.g., QS21), MDP derivatives, CpG oligos, LPS, MPL, polyphosphazenes, emulsions (e.g., Freund's, SAF), liposomes, virosomes, iscoms, cochleates, PLG microparticles, poloxamer particles, virus-like particles, heat-labile enterotoxin (LT), cholera toxin (CT), mutant toxins (e.g., LTK63 and LTR72), microparticles and/or polymerized liposomes may be used.

According to a preferred embodiment of the present invention the peptide is formulated with an adjuvant, preferably adsorbed to alum.

In a related embodiment, the invention is useful for the prevention or treatment of diseases, disorders or conditions associated with the RAS, including but not limited to hypertension, stroke, infarction, kidney failure, congestive heart failure, vascular damage or retinal hemorrhage. In addition to that immunization using peptides enclosed in the embodiment of the present invention can be used to treat or prevent atherosclerotic plaque formation, arterial thrombosis events and events associated with vascular inflammation. Beside this treatment of autoimmune diseases such as multiple sclerosis can be performed using peptides enclosed in the embodiment of the present invention.

The vaccine of the present invention may be administered subcutaneously, intramuscularly, intradermally, intravenously (see e.g. "Handbook of Pharmaceutical Manufacturing Formulations", Sarfaraz Niazi, CRC Press Inc, 2004). Depending on the route of administration, the medicament may comprise respective carriers, adjuvants and/or excipients.

The vaccine according to the present invention contains the compound according to the invention in an amount of from 0.1 ng to 10 mg, preferably 10 ng to 1 mg, in particular 100 ng to 100 µg, or, alternatively, e.g. 100 fmol to 10 µmol, preferably 10 µmol to 1 µmol, in particular 100 µmol to 100 nmol. The compound or peptide of the present invention is administered to a mammal in an amount of preferably 100 ng to 1 mg, more preferably 1 µg to 500 µg, even more preferably 10 µg to 100 µg, in particular 20 to 40 or 30 µg, per doses. Typically, the vaccine may also contain auxiliary substances, e.g. buffers, stabilizers etc.

Yet, another aspect of the present invention relates to the use of a peptide according to the present invention for the manufacture of a medicament for treating and/or preventing physical disorders associated with the renin-activated angiotensin system, preferably hypertension and hypertension-associated diseases.

The abbreviations for the amino acid residues disclosed in the present invention follow the IUPAC recommendations:

| Amino Acid | 3-Letter Code | 1-Letter Code |
|---|---|---|
| Alanine | Ala | A |
| Arginine | Arg | R |
| Asparagine | Asn | N |
| Aspartic | Asp | D |
| Cysteine | Cys | C |
| Glutamic | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

EXAMPLES

Example 1

Positional-Scanning of the Ang II Peptide

Angiotensin II (Ang II), a key component of the blood pressure regulating RAS was chosen as target for a vaccination approach. Therefore, peptides which are able to induce a humoral immune response that targets angiotensin II have been identified and selected.

The term "positional scanning" refers to a technology that systematically substitutes the amino acid (AA) residues at each position within a certain protein or peptide region with other AAs. This technology has been used and applied so far only for protein-protein interaction studies, peptide-protein interaction studies and/or for studying the functionality of peptide or protein domains.

The positional scanning technology was now transferred into and applied in the field of immunology to identify appropriate VARIOTOPEs for the octapeptide Ang II (DRVYI-HPF) (SEQ ID NO:4). The aim of this example was to identify AA for each position that support or at least do not interfere with the induction of a polyclonal/oligoclonal humoral immune response that targets the Ang II peptide.

Therefore, in a first set of experiments each position in the Ang II sequence was systematically replaced by amino acids having similar or different features (see Table 1 for position 2). Subsequently all these peptides were chemically linked via an additional N-terminal cysteine to the protein carrier keyhole limpet haemocyanin (KLH) and administrated to mice (BALB/c) together with Alum as adjuvant. Sera from vaccinated mice were used to analyze the immunogenicity of indicated peptides. For this purpose a peptide based ELISA assay was used to define sera titers against the injected peptide (i.e. Ang II peptide variants, VARIOTOPEs) as well as to define the binding capacity of the obtained sera against the Ang II peptide.

TABLE 1

Peptide variants by amino acid substitution for position 2

| 1 2 3 4 5 6 7 8 | Position | | | |
|---|---|---|---|---|
| C D R V Y I H P F | Ang II | | | SEQ ID NO: 235 |
| C D A V Y I H P F | aliphatic | non-polar | neutral | SEQ ID NO: 236 |
| C D E V Y I H P F | opposed charge | polar | acidic | SEQ ID NO: 237 |

TABLE 1-continued

Peptide variants by amino acid substitution for position 2

| 1 2 3 4 5 6 7 8 | Position | | | | |
|---|---|---|---|---|---|
| C D F V Y I H P F | aromatic | non-polar | neutral | SEQ ID NO: | 238 |
| C D H V Y I H P F | aromatic | polar | basic | SEQ ID NO: | 239 |
| C D K V Y I H P F | aliphatic | polar | basic | SEQ ID NO: | 240 |
| C D M V Y I H P F | aliphatic | non-polar | neutral | SEQ ID NO: | 241 |
| C D V V Y I H P F | aliphatic | non-polar | neutral | SEQ ID NO: | 242 |
| C D Y V Y I H P F | aromatic | polar | neutral | SEQ ID NO: | 243 |
| C D P V Y I H P F | ring | non-polar | neutral | SEQ ID NO: | 244 |

In the Figures (FIGS. 1 to 8 for position 1 to position 8) the results derived from these experiments are shown. On the X-axis sera derived from animals immunized with indicated peptides are listed. On the Y-axis relative titers of induced sera are shown. Titers derived from Ang II treated animals were set as 100%. Titers were calculated as the sera dilution giving half-maximal binding (i.e. $OD_{max}/2$). White bars indicate titers against the peptides that were used for vaccination while black bars represent titers against the Ang II peptide.

Although all tested Ang II peptide variants for position 1 were able to induce antibodies which bound to the injected peptide (FIG. 1), indicating that the amino acid exchange did not abrogate their immunogenicity completely, some peptide variants induced sera that showed a significantly lower titer (peptide variants having an aromatic amino acid exchange). In contrast to this, the peptide variant with G on position 1 seems to have the capacity to induce sera-titers against the injected peptide that are almost twice as high as sera-titers derived from Ang II treated animals. Reactivity against Ang II is roughly increased by 50% using this variant. Sera derived from peptide variants containing A, T, E, N, R or H on first position do not differ significantly from sera derived from Ang II peptide. Aromatic or aliphatic residue on position 1 such as L, F, Y seem to be less favorable for inducing an immune response that recognizes Ang II.

Therefore, position 1 may contain the following AA:
the original AA D
the amino acids G, A
amino acids that are polar such as E, N, R, H.

Figure 2:
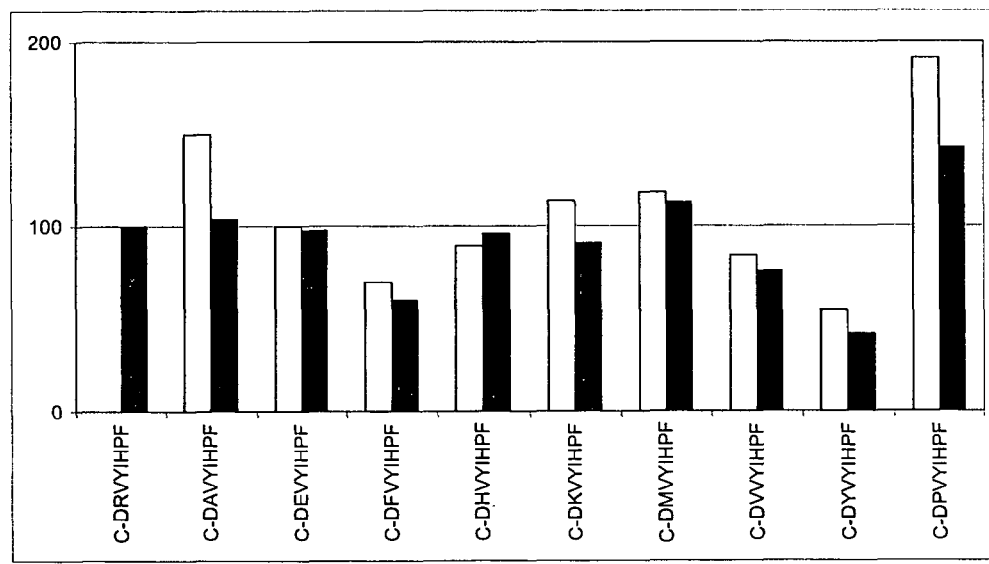
FIG. 2 shows the immunogenicity of peptide variants for position 2 of Ang II peptide CDRVYIHPF (SEQ ID NO:235).
Figure 3:
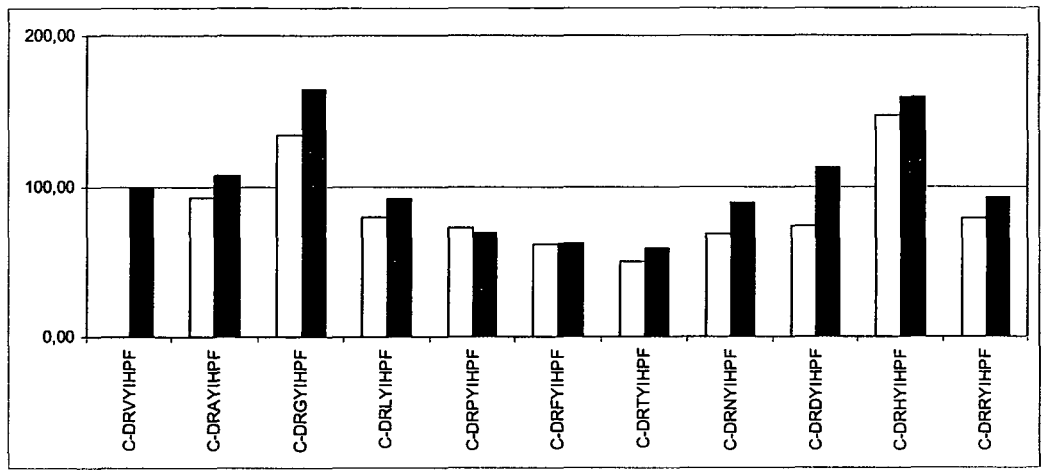
FIG. 3 shows the immunogenicity of peptide variants for position 3 of Ang II peptide CDRVYIHPF (SEQ ID NO:235).
Figure 4:
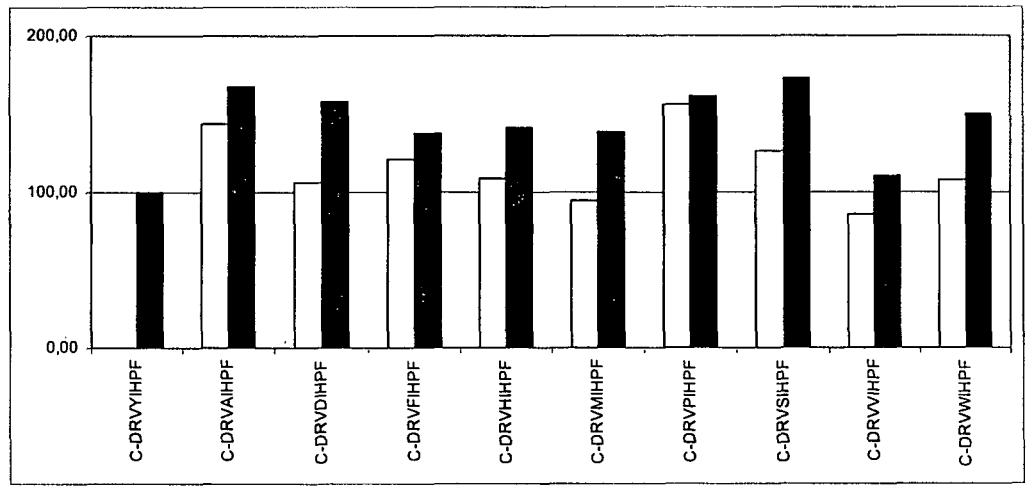
FIG. 4 shows the immunogenicity of peptide variants for position 4 of Ang II peptide CDRVYIHPF (SEQ ID NO:235).
Figure 5:
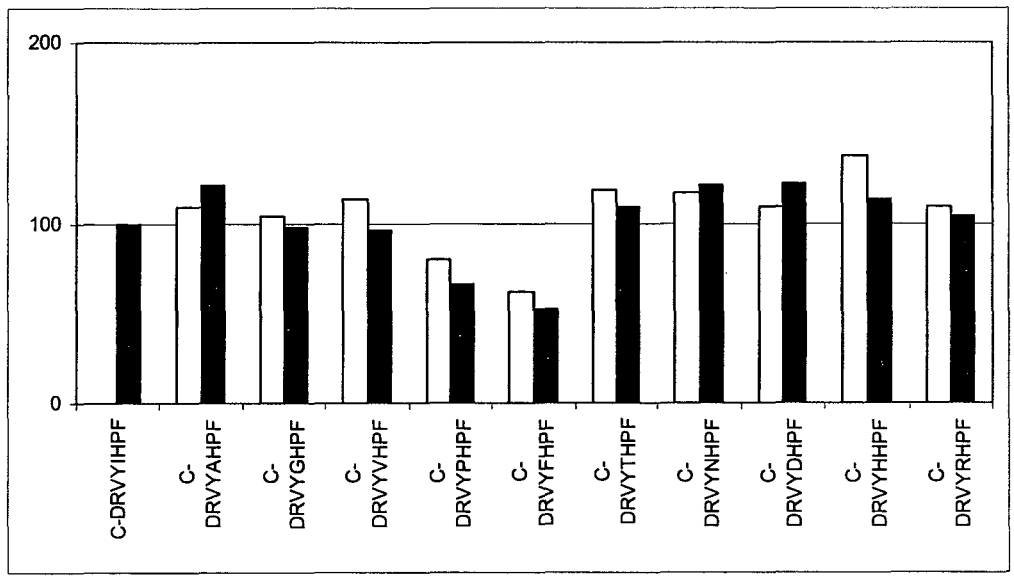
FIG. 5 shows the immunogenicity of peptide variants for position 5 of Ang II peptide CDRVYIHPF (SEQ ID NO:235).

As outlined in FIG. 2 using peptides for immunization where the arginine on position 2 was replaced by P or M increased the titer and also the reactivity to Ang II. Peptides with e.g. R to A or R to K substitution evoked sera that showed the same titer as sera induced by the Ang II peptide. These results indicate that a P or M instead of an R on position 2 is more favorable for inducing a humoral immune response. A and K for example seem to be as good as R.

Position 2 may contain the following AA:
the original AA R
the non-polar and neutral AAs P, M, G and A
amino acids that are polar such as E, H, K
Position 3 may contain following AA:
the original AA V
The AAs G and H (most favorable)
non-polar and neutral AAs such as A
AA aliphatic AA such as L
amino acids that are polar such as E, H, K On Position 4 the original AA Y can be substituted by all AA irrespective of their characteristics.

The aromatic AAs Y and W and the AA P cannot substitute the original AA I on position 5. All other AA can be used for this purpose.

Figure 6:
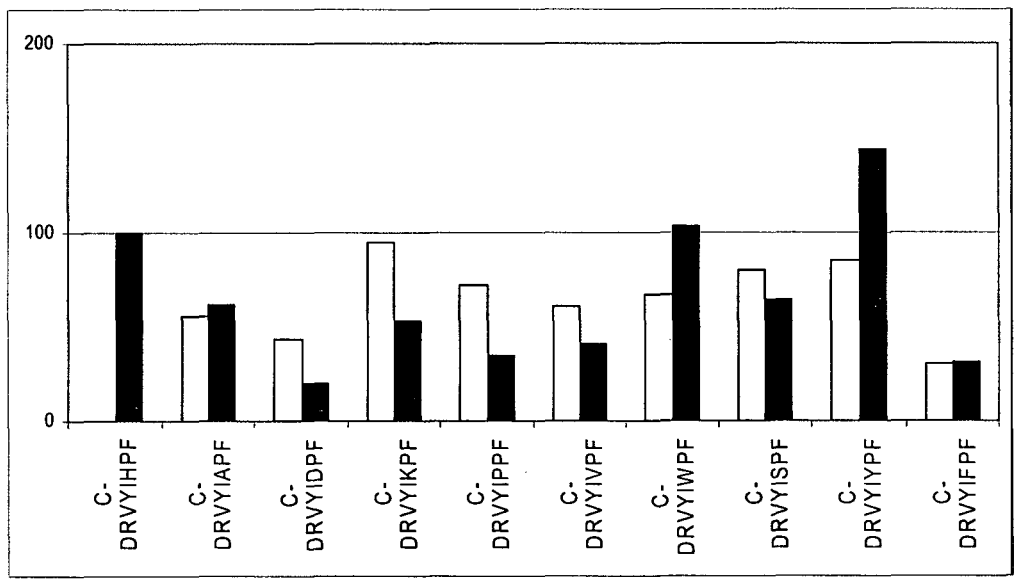
FIG. 6 shows the immunogenicity of peptide variants for position 6 of Ang II peptide CDRVYIHPF (SEQ ID NO:235).

The results derived from peptides where the H on position 6 was replaced by indicated amino-acids are shown in FIG. 6. Substitution of the aromatic amino-acid H by other aromatic amino acids such as W, and Y resulted in peptides that have the capacity to induce sera that seem to recognize Ang II even better than the peptide used for vaccination. For peptides with non aromatic amino-acid substitutions on position 6 the reactivity of evoked sera to Ang II is considerably diminished (up to 60%). These results indicate that on position 6 aromatic amino acid can be placed (but not F).

Position 6 may contain following AA:
the original AA H
amino acids that contain an aromatic side chain such as Y, W
Position 7 may contain following AA:
the original AA P
alternatively amino acids that contain an aromatic side chain such as F, W, H may potentially be used
Position 8 may contain following AA:
the original AA F
the AA A, L, I, V, P, M Example 2

Combined Exchanges of Two or More AA–Positions in Ang II Sequence Using Alanine

Figure 7:
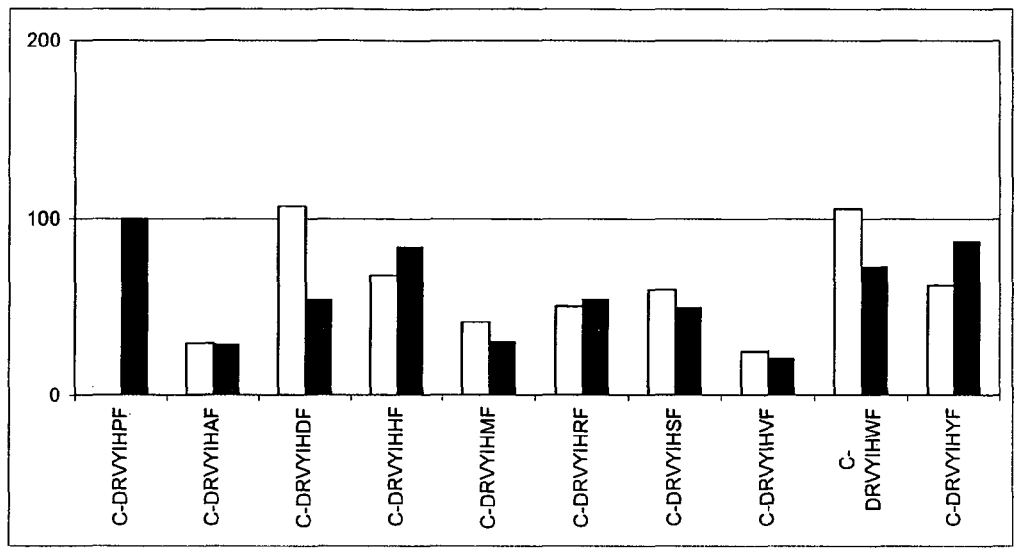
FIG. 7 shows the immunogenicity of peptide variants for position 7 of Ang II peptide CDRVYIHPF (SEQ ID NO:235).
Figure 8:
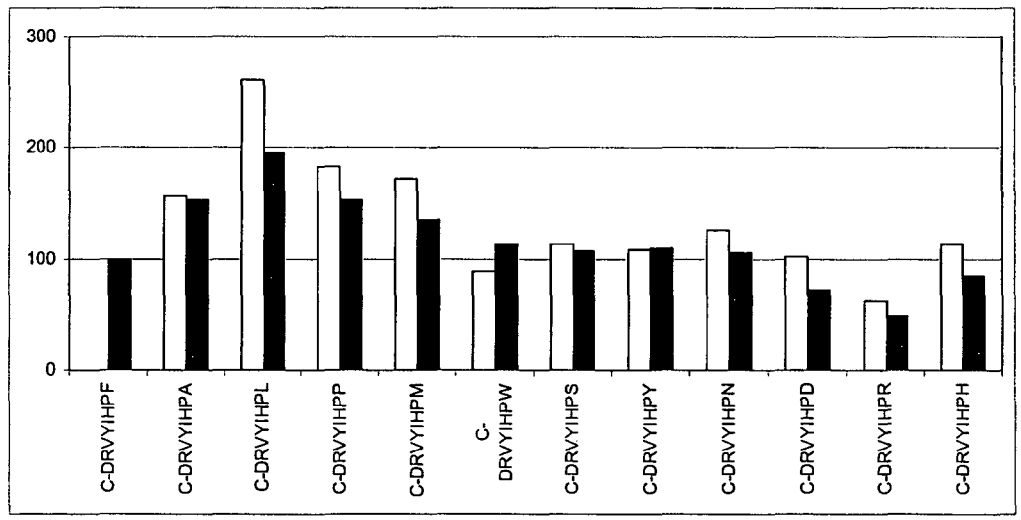
FIG. 8 shows the immunogenicity of peptide variants for position 8 of Ang II peptide CDRVYIHPF (SEQ ID NO:235).
Figure 9:
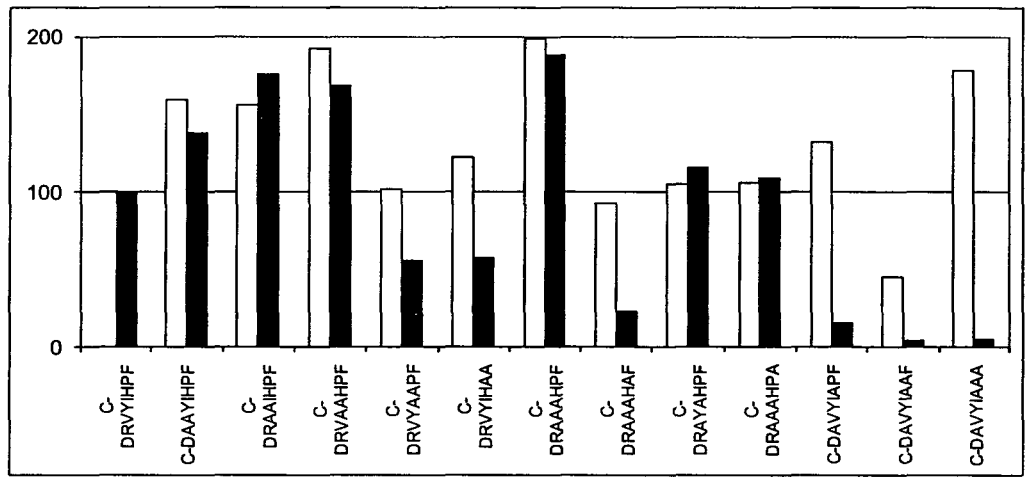
FIG. 9 shows the immunogenicity of peptide variants where two or more amino acids were replaced by alanine.

To prove the results derived from the first in vivo experiments where the positional scanning approach was performed, and to test whether combined AA exchanges on different positions might either be additive, when neutral or favorable AA replace the original AA, or subtractive, when less favorable AA are combined, two or more amino acids in the Ang II sequence were replaced. For this purpose in a next set of experiments the amino acid alanine was used (Table 2). Alanine has been defined as a favorable-exchange AA for position 4 (FIG. 4), a neutral-exchange AA for position 1, 2, 3, 5, and for position 8 (FIGS. 1 to 3, 5, 8 and 9). For position 6 and 7 the exchange of the original AAs H and P, respectively, to alanine appeared to be less favorable (FIGS. 6, 7 and 9). Therefore, peptide variants containing alanine on position 4 (favorable exchange) in combination with 1 to 3, 5, and 8 (neutral exchange), can be expected to induce titers against Ang II that are higher or have at least the same value as titers from sera evoked by Ang II peptide. Peptide variants containing alanine on position 1 to 3, 5 and 8 should induce at least an immune response that recognizes Ang II equally well as sera evoked by Ang II peptide. Peptide variants with alanine exchanges on position 6 and 7 (less favorable exchange amino acid for these positions) can be expected to evoke sera with diminished reactivity against Ang II.

All peptides listed in Table 2 were again chemically linked via the N-terminus to KLH adsorbed to Alum and injected s.c. into experimental animals (BALB/c mice). Sera were analyzed by ELISA and antibody responses induced by the peptide variants were compared to that one induced by the original peptide.

TABLE 2

Example for peptide variants by amino acid substitution

| sequence | exchanged position | exchanged amino acid |
|---|---|---|
| C-DRVYIHPF (SEQ ID NO: 235) | | |
| C-DAAVIHPF | 2, 3 | R, V |
| C-DRAAIHPF | 3, 4 | V, Y |
| C-DRVAAHPF | 4, 5 | Y, I |
| C-DRVYAAPF | 5, 6 | I, H |
| C-DRVYIHAA | 7, 8 | P, F |
| C-DRAAAHPF | 3, 4, 5 | V, Y, I |
| C-DRAYAHPF | 3, 5 | V, I |
| C-DRAAAHPA | 3, 4, 5, 8 | V, Y, I, F |
| C-DAVYIAPF | 2, 6 | R, H |
| C-DAVYIAAF | 2, 6, 7 | R, H, P |
| C-DAVYIAAA | 2, 6, 7, 8 | R, H, P, F |

All alanine-substituted peptide variants were able to induce antibodies which bind to the injected peptide, indicating that the amino acid exchange did not abrogate their immunogenicity (FIG. 9). But the titers of the sera induced by C-DAVYIAAF, are lower compared to the titers induced by the other antigens, indicating that the combined exchange of indicated AA by alanine is less favorable for immunogenicity of the peptides (FIG. 9).

Analyzing the reactivity of peptide variant-induced sera (Table 2) against Ang II revealed that sera induced by the following peptides showed diminished reactivity to Ang II: C-DRVYAAPF, C-DRVYIHAA, C-DRAAAHAF, C-DAVY-IAPF, C-DAVYIAAF, C-DAVYIAAA, (FIG. 9). These results indicate that Ang II-peptide-variants having at least one alanine substitution at position 6 or position 7 (alanine as a non-favorable AA exchange for these positions), induce sera that show diminished reactivity to Ang II. This is in line with results obtained in positional scanning experiments.

Alanine substitutions on the position 1-5 of the Ang II molecule (for those positions A has been defined as neutral or favorable AA exchange) do not interfere with reactivity to Ang II. Alanine-substitution on these positions led to the induction of titers which were above to that obtained with Ang II. This effect was seen especially when Y at position 4 was replaced by alanine (FIG. 9).

Investigation of various alanine-modified Ang II epitopes in Wistar rats showed similar results. This indicates that the results are not only restricted to mice but can also be transferred to another species.

Example 3

Figure 10:
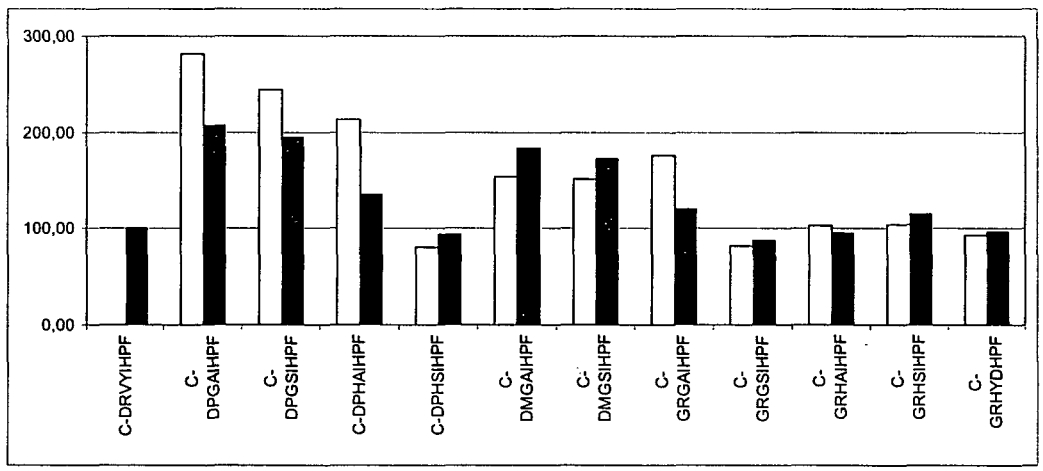
FIG. 10 shows the immunogenicity of peptide variants where three amino acids were replaced on different positions using favorable amino acid substitutes for these positions.
Figure 11:
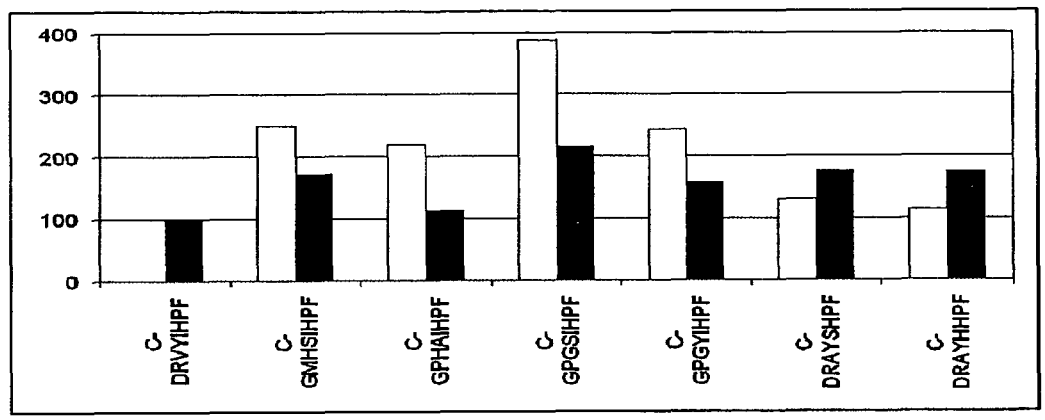
FIG. 11 shows the immunogenicity of peptide variants where two to four amino acids were replaced on different positions using favorable amino acid substitutes for these positions.

Combination of Favorable AAs on Different Positions for Selection of Angiotensin VARIOTOPEs In next experiments AA combinations of favorable and/or neutral AA for each position have been tested. As can be seen in FIGS. 10 and 11 amino acid exchanges on different positions using favorable amino acids selected during positional scanning experiments result in the formation of VARI-OTOPEs that are able to induce humoral immune responses to angiotensin II that are comparable or higher to that response induced by angiotensin II.

Example 4

Figure 12:
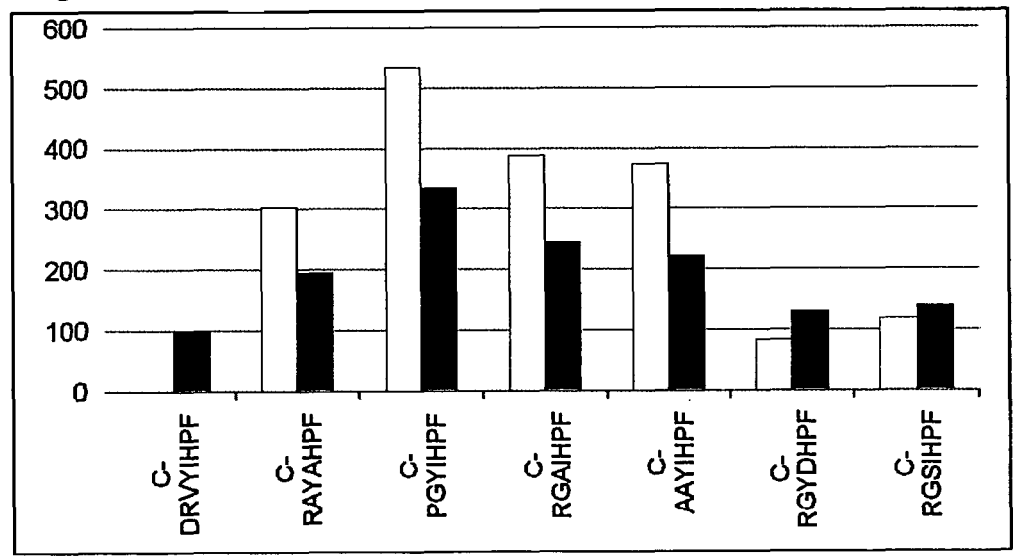
FIG. 12 shows the immunogenicity of truncated angiotensin VARIOTOPE versions missing the first N-terminal amino acid.
Figure 13:
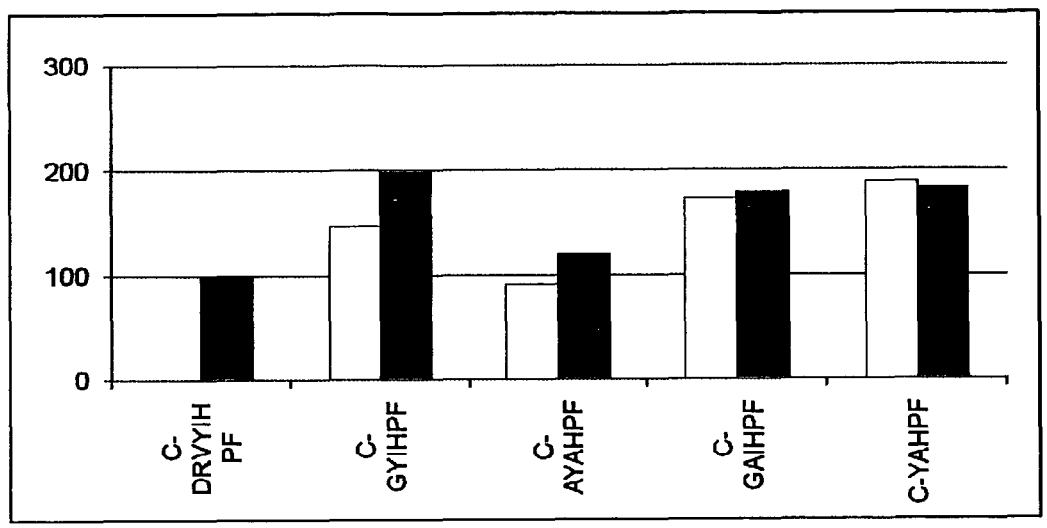
FIG. 13 shows the immunogenicity of truncated angiotensin VARIOTOPE versions missing the first two or three N-terminal amino acids.

Truncated Angiotensin VARIOTOPE Versions Missing the First N-Terminal Amino Acid Residues In next experiments truncated versions of angiotensin VARIOTOPEs have been tested. As can be seen in FIGS. 12 and 13 shortening angiotensin VARIOTOPEs (selected as outlined above) on their N-termini does not abrogate their capacity to induce humoral immune responses to angiotensin II that are comparable or higher to that response induced by angiotensin II.

The invention claimed is:

1. A pharmaceutical composition for inducing an immune response comprising a peptide bound to a pharmaceutically acceptable carrier, wherein said peptide comprises a sequence selected from the group consisting of DPVYIHPF (SEQ ID NO:7), DAVYIHPF (SEQ ID NO:10), DRHYIHPF (SEQ ID NO:13), DAAYIHPF (SEQ ID NO:27), DRAYAHPF (SEQ ID NO:30), DPGYIHPF (SEQ ID NO:39), DRAYDHPF (SEQ ID NO:58), AAYIHPF (SEQ ID NO: 111), RAYAHPF (SEQ ID NO: 114), PGYIHPF (SEQ ID NO:164), wherein the pharmaceutical composition for inducing an immune response is for treating a physical disorder associated with the renin-activated angiotensin system.

2. The pharmaceutical composition according to claim 1, characterised in that at least one cysteine residue is bound to the N-terminus of the peptide.

3. The pharmaceutical composition according to claim 1, characterised in that the carrier is a protein carrier.

4. The pharmaceutical composition according to claim 3, characterised in that the protein carrier is selected from the group consisting of keyhole limpet haemocyanin (KLH), tetanus toxoid (TT) and diphtheria toxin (DT).

5. The pharmaceutical composition according to claim 1, characterised in that the peptide is formulated with an adjuvant.

6. The pharmaceutical composition according to claim 1, characterised in that the physical disorder associated with the renin-activated angiotensin system is selected from the group consisting of hypertension, stroke, infarction, kidney failure, congestive heart failure, atherosclerosis, vascular damage, retinal hemorrhage and an autoimmune disease wherein the autoimmune disease is multiple sclerosis.

7. A method of inducing an immune response for treating a physical disorder associated with the renin-activated angiotensin system in a mammal comprising administering to the mammal the pharmaceutical composition according to claim 1.

8. The method of claim 7, wherein the physical disorder is selected from the group consisting of hypertension and hypertension-associated disease.

9. The pharmaceutical composition of claim 5, wherein the peptide is adsorbed to alum.

* * * * *